(12) United States Patent
Lee et al.

(10) Patent No.: US 9,816,086 B2
(45) Date of Patent: Nov. 14, 2017

(54) DOSE AND LOCATION CONTROLLED DRUG/GENE/PARTICLE DELIVERY TO INDIVIDUAL CELLS BY NANOELECTROPORATION

(71) Applicant: The Ohio State University, Columbus, OH (US)

(72) Inventors: Ly James Lee, Columbus, OH (US); Pouyan E. Boukany, Columbus, OH (US); Jingjiao Guan, Tallahassee, FL (US); Nan-Rong Chiou, Midland, MI (US)

( * ) Notice: Subject to any disclaimer, the term of this patent is extended or adjusted under 35 U.S.C. 154(b) by 472 days.

(21) Appl. No.: 14/282,630

(22) Filed: May 20, 2014

(65) Prior Publication Data

US 2014/0256047 A1 Sep. 11, 2014

Related U.S. Application Data

(62) Division of application No. 13/177,514, filed on Jul. 6, 2011, now abandoned.

(60) Provisional application No. 61/361,845, filed on Jul. 6, 2010.

(51) Int. Cl.
  *C12N 13/00* (2006.01)
  *C12N 15/87* (2006.01)
  *C12M 1/42* (2006.01)

(52) U.S. Cl.
  CPC .............. *C12N 13/00* (2013.01); *C12M 35/02* (2013.01); *C12N 15/87* (2013.01)

(58) Field of Classification Search
  CPC ......... C12M 35/02; C12N 13/00; C12N 15/87

USPC .................. 435/7.2, 73.6, 283.1, 285.1, 461
  See application file for complete search history.

(56) References Cited

U.S. PATENT DOCUMENTS

| 5,173,158 | A | * | 12/1992 | Schmukler | ............. | C12M 35/02 |
| | | | | | | 435/173.6 |
| 6,645,757 | B1 | * | 11/2003 | Okandan | ................ | C12M 35/02 |
| | | | | | | 204/164 |
| 6,863,833 | B1 | | 3/2005 | Bloom et al. | | |
| 7,358,077 | B2 | * | 4/2008 | Zimmermann | ........ | C12M 35/02 |
| | | | | | | 435/173.6 |

(Continued)

FOREIGN PATENT DOCUMENTS

WO 2008039579 A2 4/2008

*Primary Examiner* — William H Beisner
*Assistant Examiner* — Danielle Henkel
(74) *Attorney, Agent, or Firm* — Standley Law Group LLP

(57) ABSTRACT

A simple and low cost method of producing sealed arrays of laterally ordered nanochannels interconnected to microchannels of tunable size, over large surface areas, is disclosed. The method incorporates DNA combing and subsequent imprinting. Associated micro and macroscale inlets and outlets can be formed in the same process or manufactured later in low cost, non-cleanroom techniques. The techniques embrace two procedures, generating DNA nanostrands and translating these strands into nanoscale constructs via imprinting. Devices incorporating the novel arrays have a first microchannel, a second microchannel and a nanochannel that is substantially linear and which defines an axis. The nanochannel is connected at its open ends to the microchannels, which are aligned along the axis. Methods for precise dose delivery of agents into cells employing the devices in nanoelectroporation methods are also disclosed.

10 Claims, 16 Drawing Sheets
(12 of 16 Drawing Sheet(s) Filed in Color)

(a)

(b)

(56) References Cited

U.S. PATENT DOCUMENTS

| | | | |
|---|---|---|---|
| 2004/0197909 A1* | 10/2004 | McKnight | B82Y 5/00 435/440 |
| 2005/0019836 A1* | 1/2005 | Vogel | G01N 33/554 435/7.2 |
| 2007/0155016 A1 | 7/2007 | Lee et al. | |
| 2007/0190031 A1* | 8/2007 | Sidhu | A61K 39/21 424/93.2 |
| 2008/0038806 A1* | 2/2008 | Fuhr | C12M 25/16 435/173.1 |
| 2008/0099336 A1 | 5/2008 | Broadley et al. | |
| 2008/0213912 A1 | 9/2008 | Randall et al. | |

* cited by examiner

DOSE AND LOCATION CONTROLLED DRUG/GENE/PARTICLE DELIVERY TO INDIVIDUAL CELLS BY NANOELECTROPORATION

CROSS-REFERENCE TO RELATED APPLICATIONS

This application is a divisional of U.S. Ser. No. 13/177,514, filed on 6 Jul. 2011 and now abandoned, which claims the benefit of U.S. 61/361,845 filed on Jul. 6, 2010. Each of the prior applications is incorporated by reference as if recited fully herein.

STATEMENT REGARDING FEDERALLY-SPONSORED R & D

This invention was made with government support under Grant No. EEC-0425626 awarded by the National Science Foundation. The government has certain rights in the invention.

TECHNICAL FIELD

The present invention is in the field of molecular delivery into cells and more particularly in the field of nano-scale transfection.

BACKGROUND

The ability to deliver precise amounts of biomolecules and nanofabricated probes into living cells offers tremendous opportunities for biological studies and therapeutic applications. It may also play a key role in the non-viral generation of engineered stem cells and induce pluripotent stem cells with high efficiency and non-carcinogenic properties.

A variety of cell transfection techniques have been developed including: viral vectors, chemical methods (e.g. complexes with lipids, calcium phosphate, polycations or basic proteins) and physical methods (e.g., particle bombardment, micro-injection and electroporation). Except for micro-injection these techniques are based on bulk stochastic processes where cells are transfected randomly by a large number of genes (>$10^8$/cell). A disadvantage of such methods is that the injected dose cannot be controlled.

Classical chemical transfection methods including lipoplex and polyplex based nanoparticles are often inefficient, and the level of cytotoxicity of many chemicals used is still unclear. In comparison, physical approaches are capable of delivering genes safely and efficiently because these methods can directly transfer naked genes into cells. Among them, biolistic transfection (i.e. hand-held gene gun) can be applied to a wide variety of cell/tissue types, but it causes significant physical damages to cells, and gold/tungsten particle carriers may have a negative impact on cell functions. Micro-injection is the most accurate and precise existing tool which has been widely used to generate transgenic animal models for biomedical research. Pronuclear micro-injection, in particular, is to inject a piece of manipulated DNA (also called "transgene") into one of the pronuclei of mouse donor zygote. The injected zygotes are then transferred into recipient surrogate mice that carry the manipulated embryos to terms. The advantage of such technique is that the gene of interest is directly and precisely delivered into mammalian cells or specific tissues via a least complicated procedure. Nevertheless, it requires specialized equipment, highly skilled practitioner; the quantity of injected cells is limited within a fixed time, and most unfortunately the efficiency is low. For instance, only about 1% of injected embryos develop into transgenic mice (10-20% of pups born), while transgenic livestock is in the range of 5-10% offspring born. On the other hand, electroporation (EP) is the most widely used method to physically transfect cells because of its technical simplicity, fast delivery, and almost no limitation for cell types and the size of delivery materials. It has been used as a research tool for investigating the biological functions of various potential therapeutic materials in stem cells and in cancer cells. In addition to in vitro study, electroporation is also used as a clinical tool for delivering anticancer drugs (e.g., bleomycin and cisplatin) for cancer therapy and DNA, RNA or DNA vaccines for gene therapy and DNA vaccination.

However, the transport of material is relatively nonspecific resulting in low cell viability and non-uniform transfection.

Bulk electroporation (BEP) is the most widely used physical method to transfect cells because of its technical simplicity, fast delivery, and almost no limitation on cell types and size. Recently, microfluidics-based electroporation (MEP) has emerged as a new technology developed by a number of researchers to transfect individual cells. In MEP, a cell is located next to a small aperture (dimensions of a few micrometers) that focuses the porating electric field to a corresponding area on the cell membrane. MEP offers several important advantages over BEP including lower poration voltages, better transfection efficiency, and a sharp reduction in cell mortality. However, the MEP delivery mechanism is similar to that in BEP: it is diffusion dominated, electric field strengths for the two processes are similar, and for large transfection agents such as nucleic acids or quantum dots, entry into the cytosol is (likely) effected through an attachment onto the outside of the cell membrane followed by an endocytosis-like process. Precise dose control has not been demonstrated using MEP.

None of the aforementioned methods has the ability to deliver a precise amount of therapeutic/detection agents to multiple cells with a wide range of cell size.

One-dimensional nanostructures such as nanochannels (and nanotubes) are characterized by extremely small transverse size and resultant high degree of spatial confinement that endow them a unique set of properties. When patterned laterally, these nanostructures are widely used as critical transport devices for a variety of applications such as sensing, nanomanipulation, and information processing. While numerous fabrication techniques have been developed, few can generate large and highly ordered arrays of both nanochannels and nanowires with no defects and low-cost. The most notable high-resolution lithographic techniques include electron beam lithography (EBL) and focused ion beam milling (FIB), but they are associated with either low throughput or high-cost. Another lithographic technique, nanoimprint lithography (NIL), is of high throughput and relatively low-cost, but it requires use of highly specialized equipment and molds prepared typically by EBL. Many inexpensive techniques have been developed, but they are inadequate in terms of high precision, low defect rate, or large area fabrication of both nanochannels/tubes and nanowires/strands. Moreover, these nanostructures need to be connected to the micro/macro scale structures, such as reservoirs and channels, to form functional devices. This is not a trivial task and the lack of a low-cost solution to this problem significantly limits the applicability of many available nanoconstructs.

SUMMARY

This and other unmet needs of the prior art are met by compounds and methods as described in more detail below.

Disclosed embodiments describe a new technology, nanochannel electroporation (NEP) and demonstrate dose control—~10%—to individual cells for a variety of transfection agents including oligonucleic acids, molecular beacons, plasmids, and quantum dots because of precise cell placement. NEP produces an intense poration over an extremely small area on the cell membrane: transfection agents are electrophoretically driven through the nanochannel, the cell membrane, and directly into the cytosol. Cell mortality from NEP is virtually zero. Small sized and delicate cells can be transfected with precise control over dosage and timing. The NEP device is potentially applicable for high-throughput applications.

In an aspect of the disclosed embodiments, a micropatterned PDMS stamp was placed on a small drop of low-cost DNA solution on a glass slide, followed by peeling off the stamp. As a result, DNA solution de-wetted the stamp surface, leaving stretched DNA on top of the microstructures and forming DNA nanostrands in the direction of de-wetting. For the formation of a nanochannel array, the DNA nanostrands on ridges were sputter-coated with gold. Next, the gold-coated nanostrands on the PDMS ridges were placed on a solid substrate. A low-viscosity resin, e.g. ethyleneglycol dimethacrylate (EGDMA), was used to fill the space between the ridges by capillary flow and then was solidified by UV-induced polymerization. The PDMS stamp was then removed, leaving the gold coated nanostrands embedded in the matrix of the cured polymer. At the same time, microchannels were formed from the molding of the microridges. The cured polymer tightly surrounds the nanostrand. To remove the gold-coated nanostrands and consequently form the nanochannels, the sample was soaked in a gold etchant.

Generally, disclosed NEP devices consist of two microchannels connected by a nanochannel. The cell to be transfected is positioned in one microchannel against the nanochannel and the other microchannel is filled with the agent to be delivered. This unique microchannel-nanochannel-microchannel design allows precision placement of individual cells. A voltage pulse(s) lasting milliseconds (ms) is delivered between the two microchannels causing transfection. In embodiments, dose control is achieved by adjusting the duration and number of pulses. Alternatively, the voltage level and/or the agent concentration can be changed.

Disclosed embodiments describe a method for the high-precision transfection of cells comprising providing a nanochannel electroporation device, the device comprising a first microchannel, a second microchannel and a nanochannel having a first opening at the first microchannel and a second opening at the second microchannel connecting and extending between the first and second microchannels; providing an agent to be transfected in the first microchannel; providing a cell to be transfected in the second microchannel; and applying a voltage across the nanochannel.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

A better understanding of the exemplary embodiments of the invention will be had when reference is made to the accompanying drawings, wherein identical parts are identified with identical reference numerals, and wherein.

DETAILED DESCRIPTION

Figure 1:
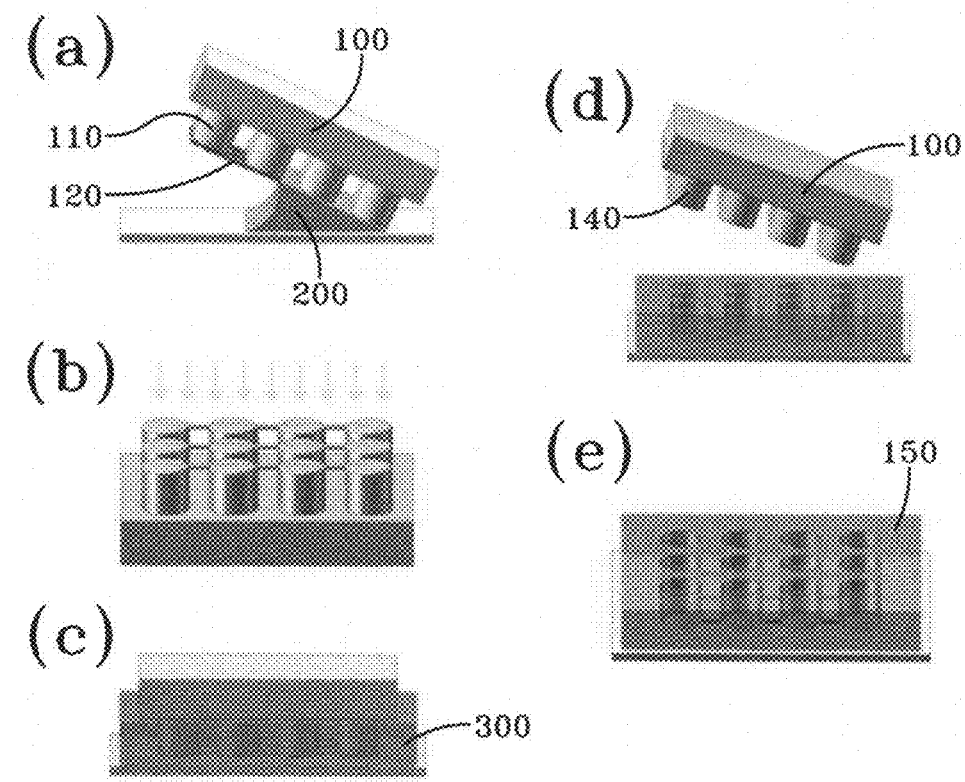
FIGS. 1a to 1e illustrate the steps of an exemplary method for the production of a nanochannel array.

The ability to deliver precise amount of biomolecules and nanofabricated probes into living cells with realtime imaging can offer unique opportunities for gene therapy, drug delivery and intercellular molecular detection.

Disclosed embodiments describe a new technology, nanochannel electroporation (NEP) and demonstrate dose control—~10%—to individual cells for a variety of transfection agents including oligonucleic acids, molecular beacons, plasmids, and quantum dots because of precise cell placement. NEP produces an intense poration over an extremely small area on the cell membrane: transfection agents are electrophoretically driven through the nanochannel, the cell membrane, and directly into the cytosol. Cell mortality from NEP is virtually zero. Small sized and delicate cells can be transfected with precise control over dosage and timing. The NEP device is applicable for high-throughput applications.

Disclosed embodiments describe a simple and low-cost DNA combing and imprinting (DCI) method capable of simultaneously forming sealed arrays of laterally ordered nanochannels interconnected to microchannels with controllable sizes and rounded shape over arbitrarily large surface areas. Associated micro- and macroscale inlets/outlets can also be formed in the same fabrication process or added later using low-cost, non-cleanroom methods. This polymer based nanoscale transport system has great potential for many challenging biomedical applications.

Disclosed methods for producing NEP devices generally embrace two procedures, generating macromolecular nanostrands and translating these strands into nanoscale constructs via imprinting. The macromolecular nanostrands are generated via a pre-patterned stamp placed in a solution of the macromolecule. The macromolecules align with the pre-patterned micro-ridges along the surface of the stamp. The stamp is then removed from the solution by first lifting one side and then the other. The peeling action, when performed along the axis defined by the macromolecule's alignment serves to remove one end of the macromolecule from the solution before the other. As the macromolecule is de-wetted from the solution it is stretched between two ridges. After de-wetting, the macromolecule-stamp construct is coated.

Once coated the stamp is used to imprint a nanochannel array. The new construct is covered in a polymer resin. The resin is cured and the stamp is removed. Due to the small size of the macromolecule, it is detached from the coated stamp when the stamp is removed, leaving a coated macromolecule stretching between adjacent apertures defined by the micro-ridges patterned on the stamp. The gold coated macromolecule is the removed by a process which leaves the newly formed polymer intact. The nanochannels are thus defined on each end by larger microchannels.

In an exemplary use of the system, the two inlets/outlets microchannels were partially sealed by a soft-sticky PDMS film. During experiments, 40 µl of a suspension containing cells in a commercial phosphate buffered solution (PBS) was loaded onto one side of the micro channel array mounted on a stage of an inverted microscope with several arms for micro-motion manipulation. Over the other side of the array, 40 µl of the PBS containing either a fluorescent dye propidium iodide (PI), an ODN, a plasmid GFP, or quantum dots (Q-dots) was loaded as model reagents for cell transfection. Two custom electrode contacts were installed on each side to generate a variety of DC pulse sequences and electric fields by using a Bio-RAD (Gene Pulser Xcell™) power supply. The microscope was employed both for visualization and to provide the tight focus required for the laser tweezers beam. About 1 W of laser power at 1064 nm was used to isolate and maneuver a single cell exemplary NEP.

FIG. 1 is a step-wise illustration of the process for producing a micro-/nanochannel array by DCI. FIG. 1a shows a patterned polymer stamp 100 being removed from a solution 200. The stamp includes a series of micro-ridges 110 arranged along a length of the stamp. In the figure, macromolecules 120 are stretched between two adjacent micro-ridges as the stamp is removed from the solution. In an embodiment, the stretching of the macromolecule is aided by the angular removal/peeling of the stamp from the solution. In an embodiment, a first end of the stamp is lifted creating tension along the macromolecule, stretching it as the macromolecule is removed from the solution. During the lifting of the stamp, the macromolecule is removed from the solution, and is de-wetted. In an embodiment, when the stamp is peeled from the solution, the peeling creates stretching of the macromolecule in the direction of the de-wetting. In an exemplary embodiment, the macromolecule may be a strand of DNA.

FIG. 1b shows an aspect of the method for producing nanochannel arrays. In an embodiment, the stamp, after having been removed from the solution is coated by a first material. In an embodiment the stamp and macromolecule are coated with gold. The coating may be performed by any known method. In an embodiment, the stamp and macromolecule are coated with gold via sputter coating.

FIG. 1c shows an aspect of the method for producing nanochannel arrays. In 1c the newly coated stamp and macromolecule are coated with a resin 300. In an embodiment, the resin is a low-viscosity resin and/or a UV curable resin. In an embodiment, the resin is ethyleneglycol dimethacrylate (EGDMA).

In FIG. 1d the stamp 100 is removed from the resin. In an embodiment, the coated macromolecule is broken from the coated micro-ridges 140 upon removing the stamp from the cured resin 300.

In FIG. 1e, the coated macromolecule is removed from the nanoarray. In an embodiment, the macromolecule is removed by chemical means including etching and dissolving of the coated macromolecule to give a micro-/nanochannel array 150.

Example

Fabrication of NEP Device

Polydimethylsiloxane (PDMS) stamps with micro-ridge designs were prepatterned with micro-ridges. Master molds for preparing the PDMS stamps were prepared using standard soft lithography by casting PDMS (Sylgard® 184. Dow Corning) prepolymer and curing agent at 10:1 weight ratio on the master. To form DNA nanostrands across the micro-ridges, a 30 µl drop of 0.5 wt % DNA (75 kbp calf thymus, USB Corp) solution in TE buffer was placed on a glass slide. The PDMS stamp was then gently placed face down on the DNA solution and immediately peeled off by pulling one end of the stamp up to produce directional stretching during the de-wetting process.

The stamp was then sputter coated with gold (Emitech K550X, Energy Beam Sciences Inc. CT, USA). The gold coated DNA nanostrands were coated with 1-octane thiol by vapor deposition to facilitate de-molding of the gold-coated stamp from the cured polymer. Specifically, stamps with the goldcoated DNA nanostrands were placed in a 10 cm-diameter Petri dish next to 5 ml 1-octane thiol. A lid was placed on the dish and 2 h were allowed for the vapor deposition of the I-octane thiol onto the gold-coated stamps.

Glass slides treated with Piranha were soaked in 2 wt % 3-trimethoxysilylpropyl methacrylate in toluene for 12 h to graft methacrylate groups on the slide surface. A stamp with micro-ridges and gold coated DNA nanostrands was placed face down on the treated glass slide. After ~2 ml of EGDMA resin (99 wt % EGDMA, 1 wt % Irgacure 651 initiator) was dropped on the slide near the stamp, the slide was placed in a vacuum desiccator. Once vacuum was established, the system was tilted to allow the EGDMA resin to flow towards the stamp. When the resin contacted the stamp, it immediately flowed into the space between the stamp and the slide by capillary forces. Vacuum was used in this process to avoid trapped air bubbles. The slide was transferred from the vacuum chamber to a small nitrogen chamber. The resin was cured using UV light (wavelength: 365 nm, intensity: 4 mW/cm2) for 20 min under nitrogen. The adhesion between the cured polymer and the glass surface was enhanced by chemical bonds between surface-grafted methacrylate groups and EGDMA. The stamp was then peeled off from the slide leaving behind the array of EGDMA micro channels connected by gold coated DNA nanostrands. To remove gold-coated nanostrands in the nanochannels, the slide was soaked in gold etchant (GE8111 Transene Company Inc., Danvers, Mass., USA) for 24 h and then thoroughly rinsed with de-ionized water leaving behind embedded nanochannels connecting the microchannels.

Example

Fabrication of NEP Device 2

A 0.5 wt % Calf thymus DNA (75 kb, USB Co) in TE buffer was prepared to produce an array of stretched DNA nanostrands on the microridge patterned PDMS stamp. The stamp was then sputter coated with gold (Emitech K550X, Energy Beam Science Inc.). The stamp with micro-patterned and gold-coated DNA nanostrands was then placed face down on a silanized glass substrate with 3-trimethoxysilylpropyl methacrylate (Sigma-Aldrich). An ethylene glycol dimethacrylate (EGDMA), (Sigma-Aldrich) resin (99 wt % EGDMA and 1 wt % lrgacure 651 initiator) was used as an imprinting resin. The resin was cured using UV light (wavelength: 365 nm, intensity: 4 mw/cm2) for 15 min under nitrogen. The stamp was then peeled off from the slide leaving behind the array of EGDMA microchannels connected by gold-coated DNA nanostrands. To remove gold-coated DNA nanostrands to form nanochannels, the slide was soaked in gold etchant (GE8111, Transene Company Inc.) for 48 hrs and then thoroughly rinsed with de-ionized (DI) water leaving behind embedded nanochannels connecting the microchannels. The chip was soaked in Piranha solution ($H_2SO_4/H_2O_2$ 7:3) for 3 hrs to make it hydrophilic. Next, the chip was rinsed with DI water for three times and soaked in 0.1% bovine serum albumin (BSA) containing DI water for 30 min to reduce the adhesion between loaded cells and substrate.

Figure 2:
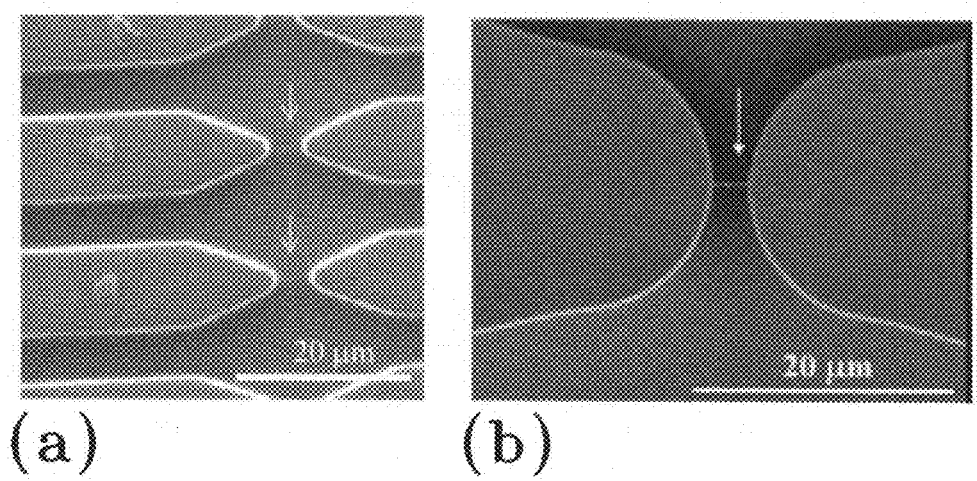
FIG. 2 shows SEM images of macromolecules arranged between microchannels.

FIGS. 2a and b are SEM images of stretched DNA nanostrands between two long micro-ridges. Arrows depict the macromolecules. FIG. 2a shows an embodiment with 6 μm ends. FIG. 2b shows an embodiment with 20 μm circular ends. These images show that the macromolecule nanostrands are oriented in the direction of de-wetting when performed in parallel to a lattice axis.

In a typical single cell BEP/MEP/NEP experiment, cells (~$10^5$ cells/mL) in suspension were centrifuged for 5 min at 5000 RPM to remove the culture medium and re-suspended in phosphate buffered saline (PBS) media for 5-10 min prior to poration. Cell manipulation was accomplished using an optical tweezers system built from a 3 W, 1064 nm laser (Crystal Lasers) and an inverted microscope (Olympus IX-71 and Nikon Eclipse TE2000). Typically, 600 mW of power was used to maneuver and hold a cell close to the tip of the nanochannel. An electron multiplying CCD camera (Photometrics Cascade II: 512 EMCCD) detected the fluorescence emission. An electronic pulser from a Bio-RAD Gene Pulser Xcell™ electroporation system was used to provide the required voltage pulse sequences. Palladium wire (0.25 mm diameter, Invitrogen/molecular probes, Eugene, Oreg.) electrodes were connected to the electronic pulser for NEP studies.

The unique microchannel-nanochannel-microchannel array design is ideal for such requirement. First, the microchannel and its curved end ensure that each cell is confined in a well defined geometry and placed at the same location against the nanochannel tip by force exerted from the optical tweezers or other hydrodynamic or mechanical means. Furthermore, the very small nanochannel tip causes minimal cell deformation when the cell is pushed against the tip.

SEM Imaging: SEM images of all samples except the nanowell/nanochannel arrays were taken in a Hitachi S-4300 SEM. The high resolution SEM images of the nanochannel were taken by a FEI Nova nanoSEM 400 equipped.

Various cell lines such as Jurkat, K562 and mouse embryonic stem cells were used and cultured in this study. Cells were maintained in T-Flask (size: 25 cm$^2$) at 37 DC with 5% $CO_2$ and subcultured and suspended in PBS buffer for EP process.

Jurkat cells (Human T cell lymphoblast-like cell line) and K562 human erythroleukemia cells were obtained from American Type Culture Collection (ATCC), (Manassas, Va.). Mouse embryonic fibroblasts (MEFs) were derived from 129/SV-E mice (Charles River Laboratories International, Inc MA, USA). Chronic lymphocytic leukemia (CLL) patient cells were provided by Dr. John Byrd's lab in the Comprehensive Cancer Center at The Ohio State University. The cells were routinely cultured in 25 T flask containing 5 mL of RPMI-1640 culture medium (Invitrogen, Grand Island, N.Y., USA) supplemented with 10% fetal bovine serum (FBS, Invitrogen 16000), 100 U/mL penicillin/100 μg/mL streptomycin (Invitrogen). The cells were seeded into T flasks at a concentration of $3 \times 10^5$ viable cells/mL, incubated at 37° C. in a humidified atmosphere containing 5% $CO_2$, and subcultured every two days.

Once fabricated, the two rows of microchannels leads to a reservoir into which cells and the transfection material may be loaded, respectively. In an exemplary embodiment, an electrode was placed in each reservoir to carry out transfection with voltage pulses between 150 and 300 volts depending on the need. An optical tweezers system was connected to the NEP construct allowing manipulation of a selected cell inside a microchannel and positioning it at the tip of the nanochannel.

Figure 3:
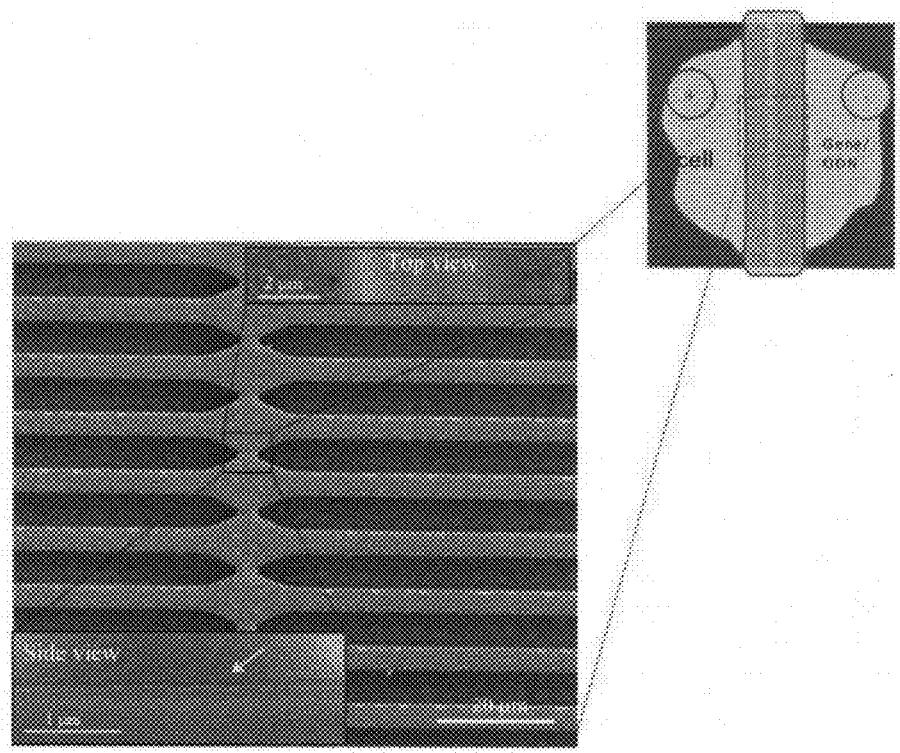
FIG. 3 is a SEM image of a nanochannel array and a schematic of a NEP chip.

An example of one of the resulting nanochannels is shown in FIG. 3 with an internal diameter around 100 nm. Disclosed embodiments of the DCI methods can produce well-defined nanochannel and micro channel arrays over an area larger than several square centimeters without any defects. Lateral nanochannels alone do not constitute a functional device. Therefore, concurrent formation of the micro channels offers significant benefits for device development. Since channel size is determined by the macromolecule size, disclosed embodiments are able to generate sealed circular nanochannels with controllable internal diameter. Since macromolecules including naked DNA nanostrands below 5 nm in thickness have been prepared by this method and polymers have been used to imprint sub-nanometer structures by the molecular imprinting technique, DCI can thus generate nanochannel arrays with a range of channel diameters from <10 to >100 nm size. The EGDMA based nanochannel/microchannel array is hydrophobic. Therefore, organic solvents and molecules can be loaded for nanoscale fluid transport and chemical reactions. For aqueous solutions the array can be soaked in Piranha solution (7:3 v/v of conc. $H_2SO_4$ and 30% $H_2O_2$) to make it hydrophilic, making the system convenient for sample loading in biomedical applications. The entire or a portion of the array surface can be covered by a soft PDMS film. This nano-featured construct can be integrated with other technologies such as micro/nano-electrodes array and magnetic or optical tweezers on an optical/fluorescent microscope to form a nano-chip platform with real-time monitoring and visualization capability. FIG. 3 also shows a schematic presentation of a NEP device capable of transfecting many individual cells with precise control of type and dosage of genes.

Figure 4:
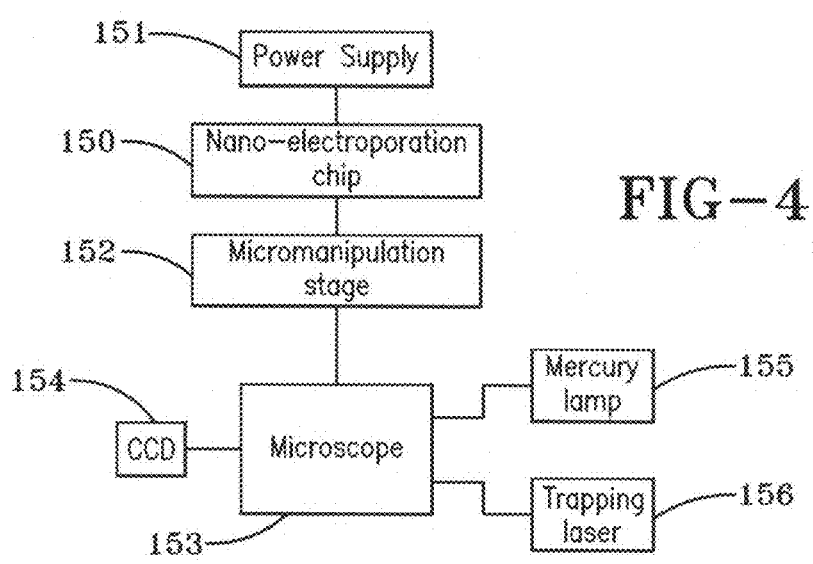
FIG. 4 is a schematic of an integrated NEP and optical tweezers system.
Figure 5:
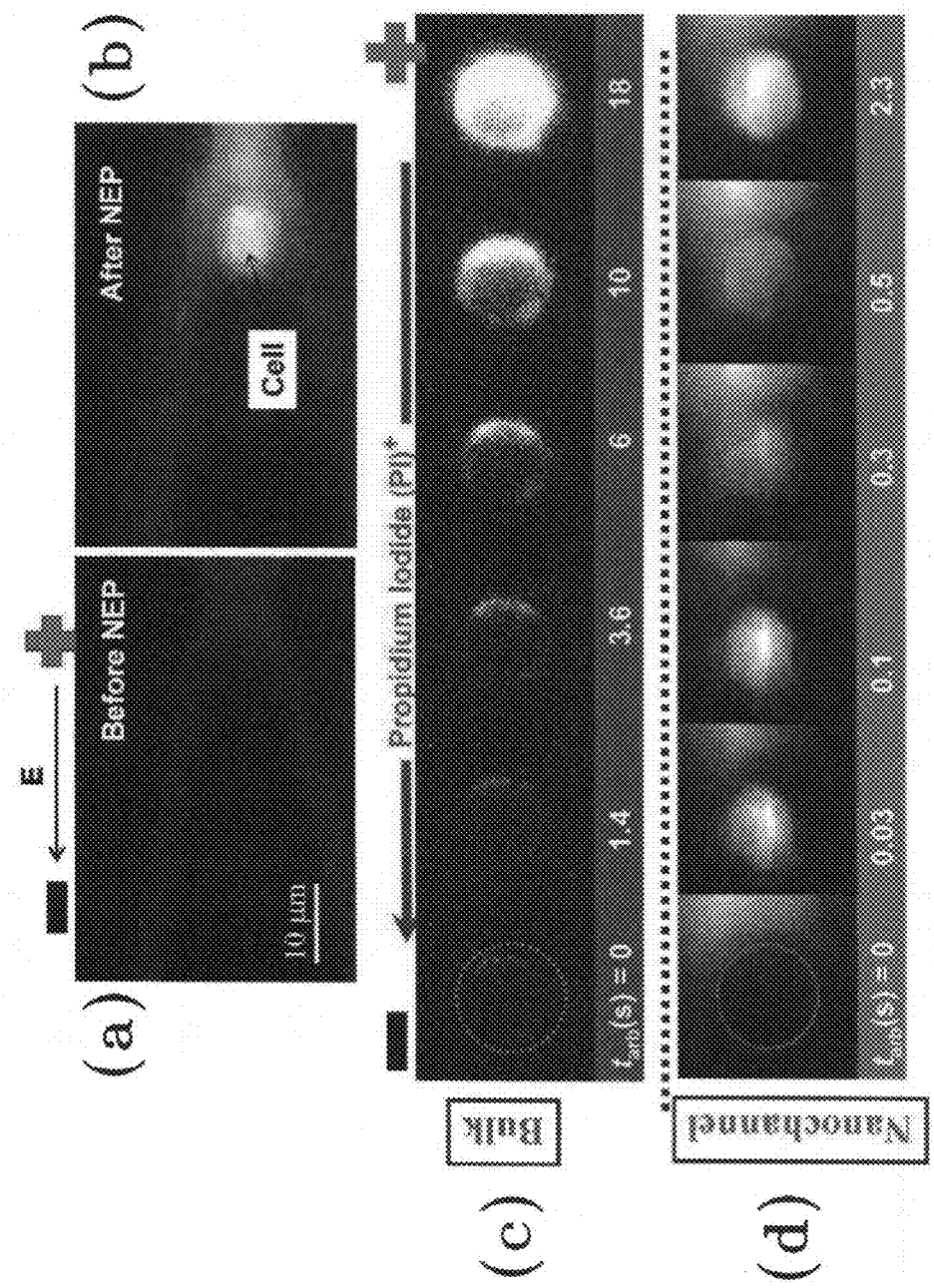
FIG. 5 is fluorescent images of PI dye transport.

FIG. 4 is a block diagram of a system to isolate and maneuver individual cells. In an embodiment, the system includes a NEP device 150, a power supply 151, a micromanipulation stage 152 a microscope 153 a COD 154 a lamp 155 and a trapping laser 156. An optical tweezers system is connected to the NEP construct allowing manipulation of a single cell inside a single micro-channel and finally holding it at the tip of the nanochannel.

Example

Electropermeabilization by PI Dye: Bulk vs. NEP

Propidium Iodide (PI) dye was used to demonstrate the concept of gene delivery by nanoelectraoporation. PI dye is a membrane impermeant dye with positive charge and low auto fluorescence. When this dye binds to the nucleic acids (DNA and RNA) in the cell, it will produce strong fluorescence (red wavelength). FIG. 5a-d is a series of pictures summarizing the uptake and time evolution of the PI in the single cell bulk EP and NEP experiments. In the case of bulk EP FIG. 5c, the gradual transfer of the PI dye (total time around 18 s) was observed after a single pulse electric bias of 700V fcm with 25 ms pulse duration, suggesting that diffusion is the dominant mechanism for PI transfer after poration. On the other hand, significant acceleration of dye transfer was observed in the case of NEP in FIG. 5d. At 0.03 s, a strong fluorescent signal is observed in the middle of the cell and after just 2.3 s the entire cell turned bright by intracellular PI dye diffusion. This observation suggests that a localized and focused eclectic field at the nanoscale can induce strong convective dye injection, resulting in the fast up-taking of the PI dye after nano-poration.

Figure 6:
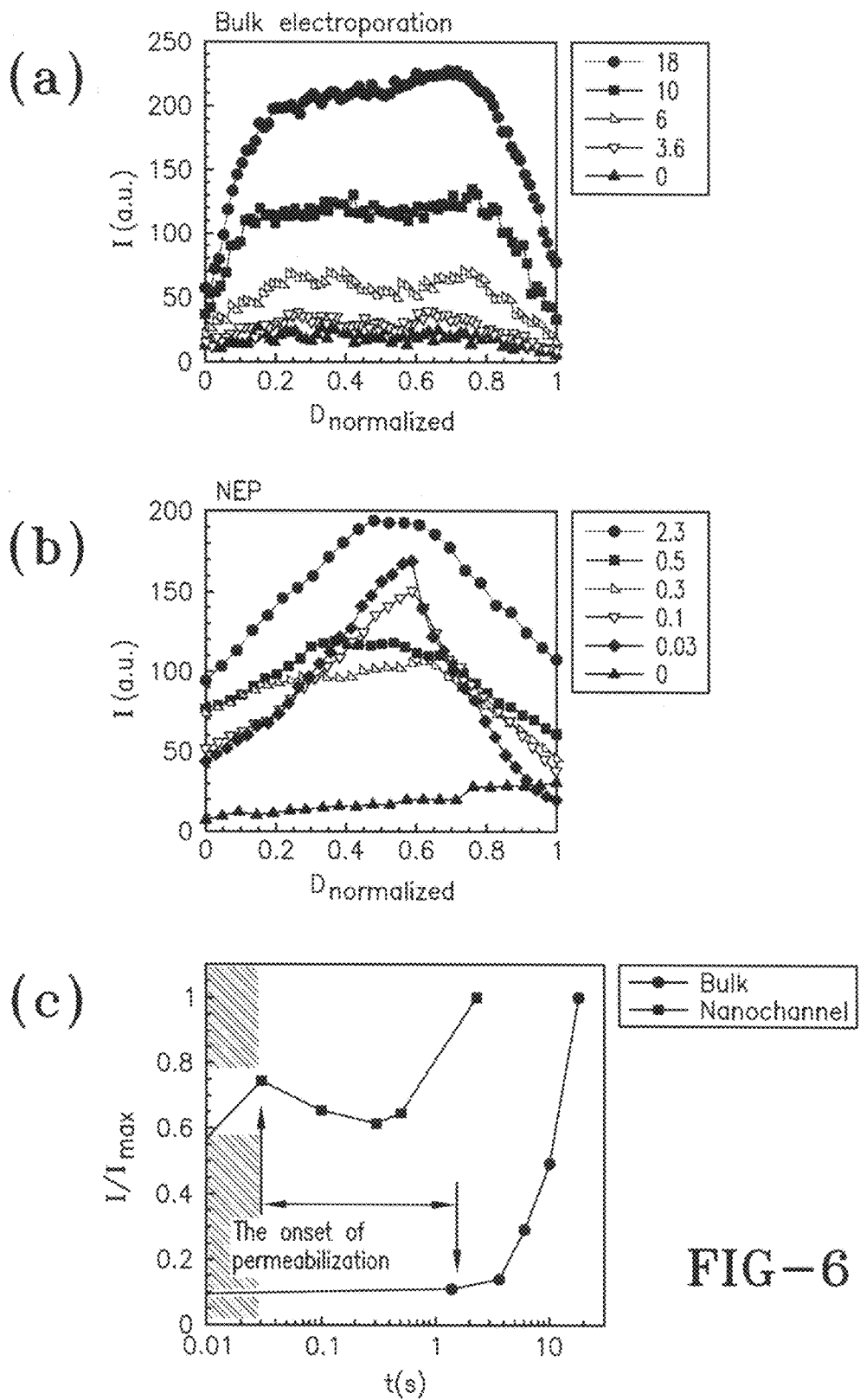
FIG. 6 is a series of graphs of fluorescent intensity profiles in cells.

FIGS. 6a-c show the results when the fluorescent intensity profiles in two cells that were measured after bulk EP and NEP. FIG. 6a shows the gradual increase of the fluorescent intensity was observed in bulk EP. On the other hand, in FIG. 6b a sharp peak of the fluorescent intensity was observed in the middle of the cell at t=0.03 ms (t=0 s is the onset of EP) in NEP, suggesting that the PI dye has been transferred into the cell by the localized high electric field near the nanochannel tip. The shape of the fluorescent intensity profile was changed from the sharp peak to smoother distribution after t>0.1 s because of internal diffusion of the PI dye inside the cell. The whole process of the PI dye up-taking in both bulk EP and NEP is summarized in FIG. 6c. Calcein acetoxymethyl ester (CaAM) was used to determine cell viability after NEP. This dye is initially non-fluorescent and cell permeable. When it diffuses across the cell membrane, the enzyme (esterase) inside the live cell will break down and convert it to the strongly green fluorescent reagent. After NEP using the PI dye, the porated cell was incubated for 30 min to fully recover cell membrane. Then, 40-50 μl of CaAM (2 μM) was introduced to the cell side. The porated cell inside the micro channel exhibited green fluorescent 30 min after applying the CaAM-containing solution. The cell viability was further confirmed by using the trypan blue dye after NEP. The trypan blue dye is unable to cross an intact live cell membrane. The porated cell by NEP did not up-take any trypan blue dye when exposed to this dye. Therefore, it was concluded that the cell is viable after the NEP treatment.

Furthermore transfection was performed with NEP, BEP and MEP of K562 cells using PI. For BEP, a single 10 ms pulse with electric field strength of 70 V/mm was used. A gradual increase of PI fluorescence (time ~150 s) was observed, indicating that diffusion after poration is the dominant mechanism for PI transfer. Similar time evolution was observed for electroporation by an MEP device. In contrast, significant acceleration of dye was observed in NEP during poration. The high velocity gained by molecules in the nanochannel allow them to be delivered into the cell during poration by a highly localized and focused electric field inducing strong electrophoresis. See Table, from left to right, NEP, MEP and BEP. This unique feature allows precise delivery of charged reagents into small cells.

| Diameter | 90 nm | 1 um | 5 um |
|---|---|---|---|
| Length | 3 um | 5 um | 5 um |
| Voltage | 180 V | 150 V | 60 V |
| Max (E) (V/m) | $5.80 \times 10^7$ | $1.60 \times 10^7$ | $1.10 \times 10^6$ |
| Drift Velocity | 0.44 m/s | 0.056 m/s | 0.0011 m/s |
| Traveling Time | 5.52 us | 32 us | 630 us |

Example ODN (20 bp) Transfection with Controlled Dosage by NEP

Figure 7:
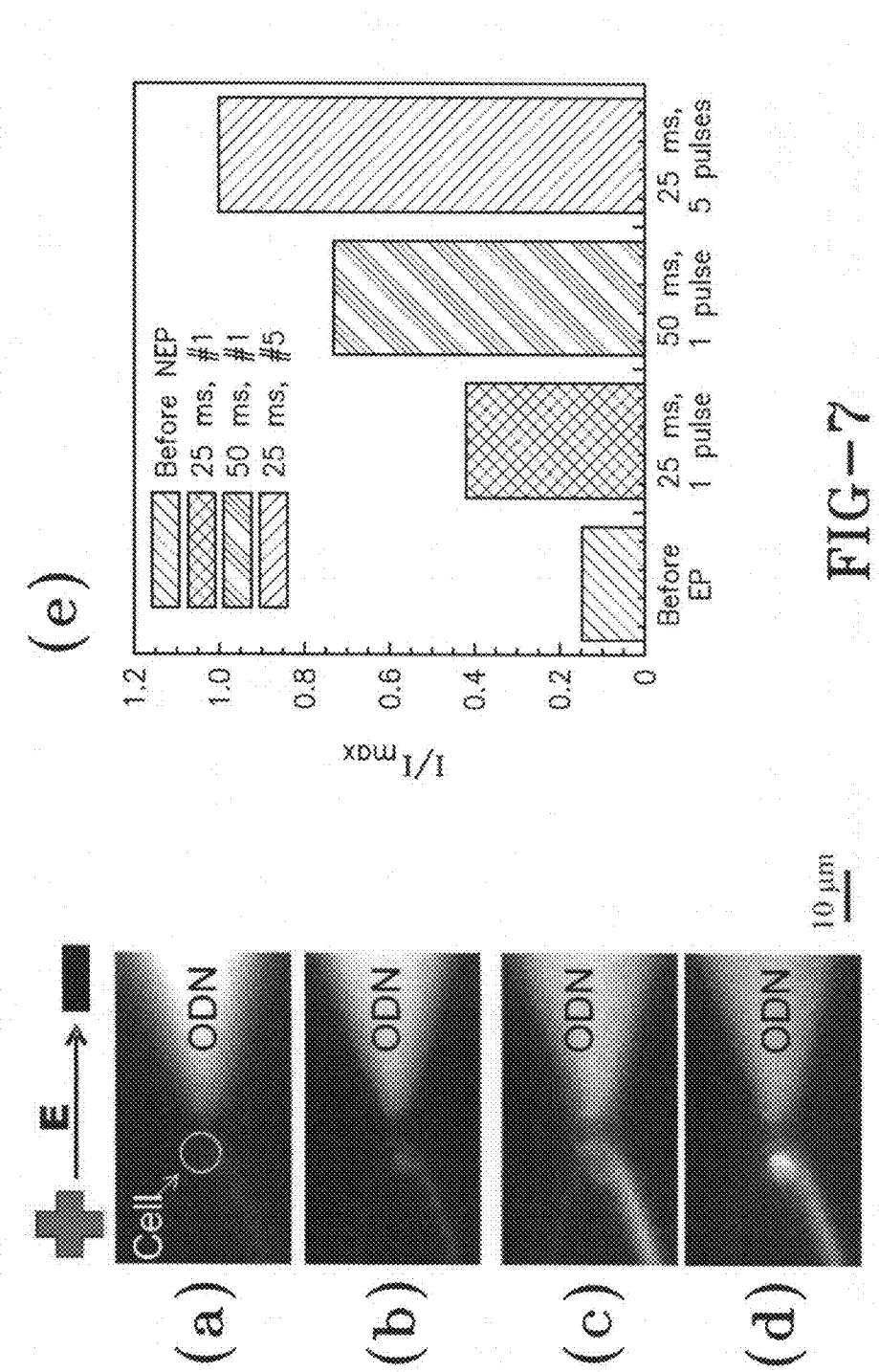
FIG. 7 show fluorescent images of a single cell inside a microchannel hold near the tip of a nanochannel and a graph of changes of normalized intensity at different NEP settings.

FIG. 7 is a series of pictures and a graph showing the results of fluorescent images of a single cell in a microchannel. A negatively charged and FITC conjugated ODN (G3139, 20 bp) was delivered by NEP. FIG. 7a shows that in the absence of any electric filed, the leukemia patient cell was not visible in the NEP device. ODN transfer into the cell was carried out by applying one pulse of 300 V/2 mm with 25 ms duration in NEP, FIG. 7b. When the pulse length was increased from 25 to 50 ms in one pulse of 300V/2 mm, the enhancement of fluorescent intensity inside the cell was observed FIG. 7c. Finally, five pulses of 25 ms at the same electric field (300 V/2 mm) were applied and the cell up-took much more ODN, resulting in a sharp increase of the fluorescent intensity FIG. 7d. The effect of different EP settings on ODN up-taking is summarized in FIG. 7e. These results demonstrate that embodiments of the NEP-device can control the dosage of small nucleic acids by adjusting the pulse duration and number of pulse. This precise control can offer opportunities to better understand the biological processes during/after gene delivery.

Example

ODN Transfection by NEP

Figure 8:
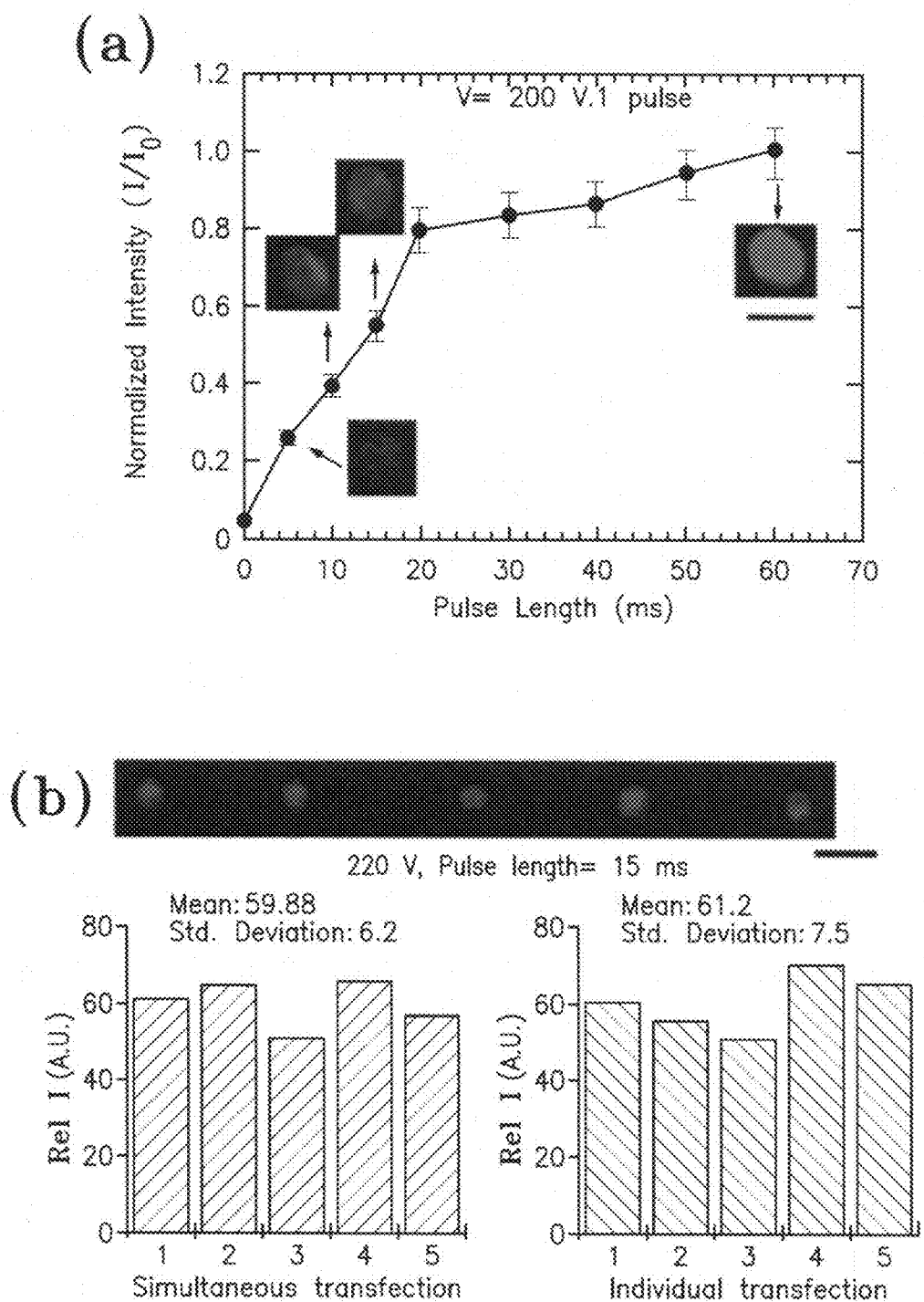
FIG. 8 shows data for dosage control studies using Jurkat cells transfected with Cy3-ODN using a single pulse.

To further show dosage control of NEP, Jurkat cells (~15 μm diameter) were transfected with an 18-mer oligodeoxynucleotide (ODN, G3139) conjugated with Cy3 to allow fluorescent detection. FIG. 8 summarizes the results of this example. NEP using a single 220 V/2 mm pulse of varying durations was carried out and the fluorescence signal from the ODN uptake was observed, measured and is summarized in FIG. 8a. The amount of ODN transfected is a monotonic function of the pulse duration and near-linear from 5 to 20 ms. Similar dose vs. pulse length dependence was also seen for Leukemia patient cells as small as 8 μm diameter. To demonstrate the reliability and repeatability of NEP, five cells were transfected either simultaneously or individually, FIG. 8b. The amount of ODN delivered showed cell to cell variation of about 10% or ±12% respectively.

Example

GAPDH Transfection

Figure 9:
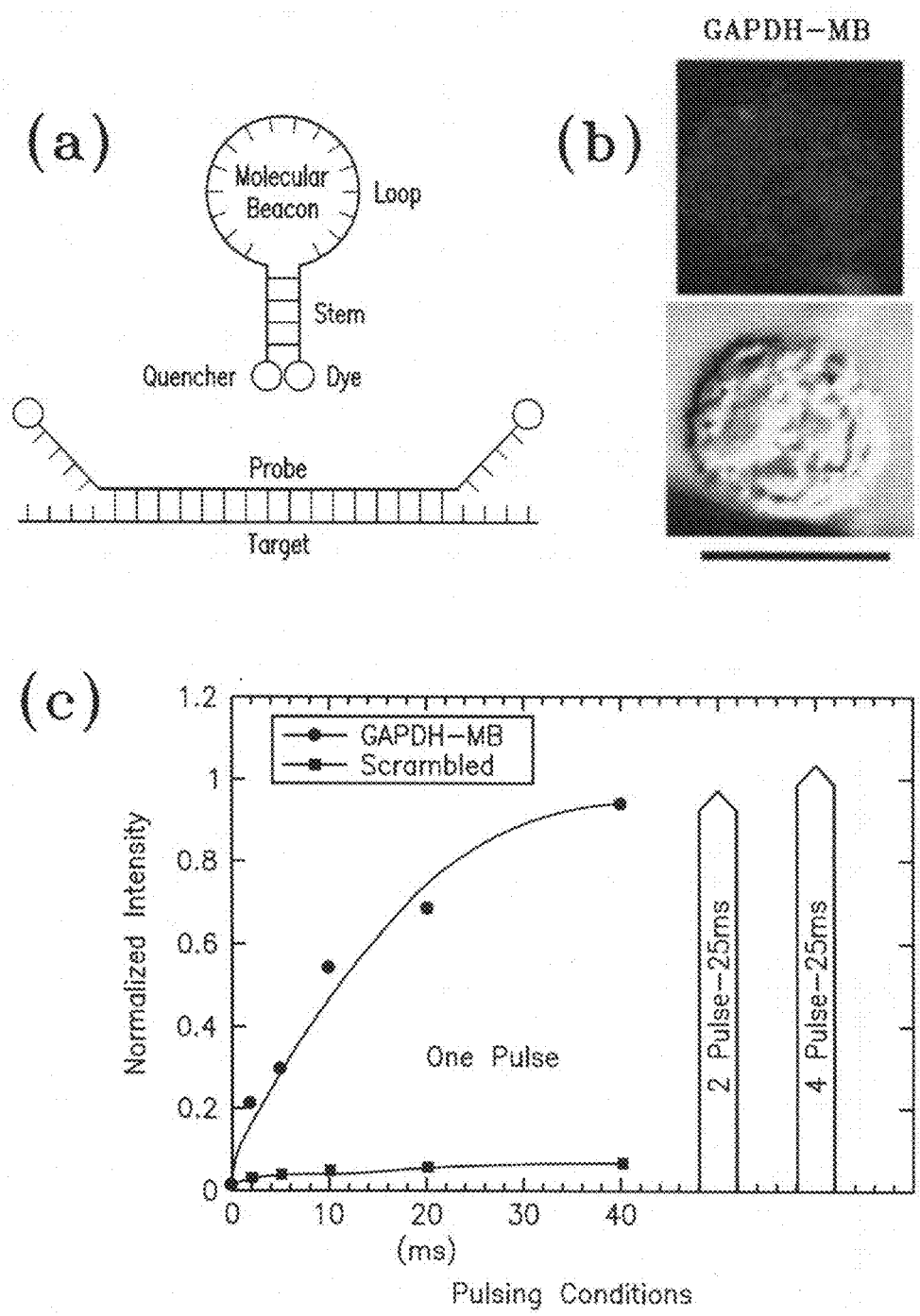
FIG. 9 shows a molecular beacon, a Jurket cell transfected with MBs producing fluorescence and a graph of relative intensities.

The delivery of a GAPDH molecular beacon (MB) by NEP was examined. GAPDH-MB is a mRNA probe having a fluorophore at one end and a quencher at the other end of a stem-hairpin structure FIG. 9a. After hybridization with complementary targets, the fluorescence is restored by separating the fluorophore and the quencher, allowing real-time expression and localization of specific mRNA inside living cells. FIG. 9b shows that successful delivery of GAPDH-MB resulted in red fluorescence inside a cell. A mismatch-MB probe (scrambled) was also transferred as negative control to confirm the selectivity of the MB. FIG. 9c summarizes the fluorescent intensity inside the cells at different conditions. FIG. 9c shows the relative fluorescence intensities measured under various conditions as 220 V/2 mm within 45 min after NEP. The plateau of GAPDH-MB signal at a long pulse lengths or multiple pulses indicates that all GAPDH in the cell were detected. Since NEP can deliver probes quickly into the cell, time-dependent fouling of MB is avoided.

Example siRNA Transfection

Figure 10:
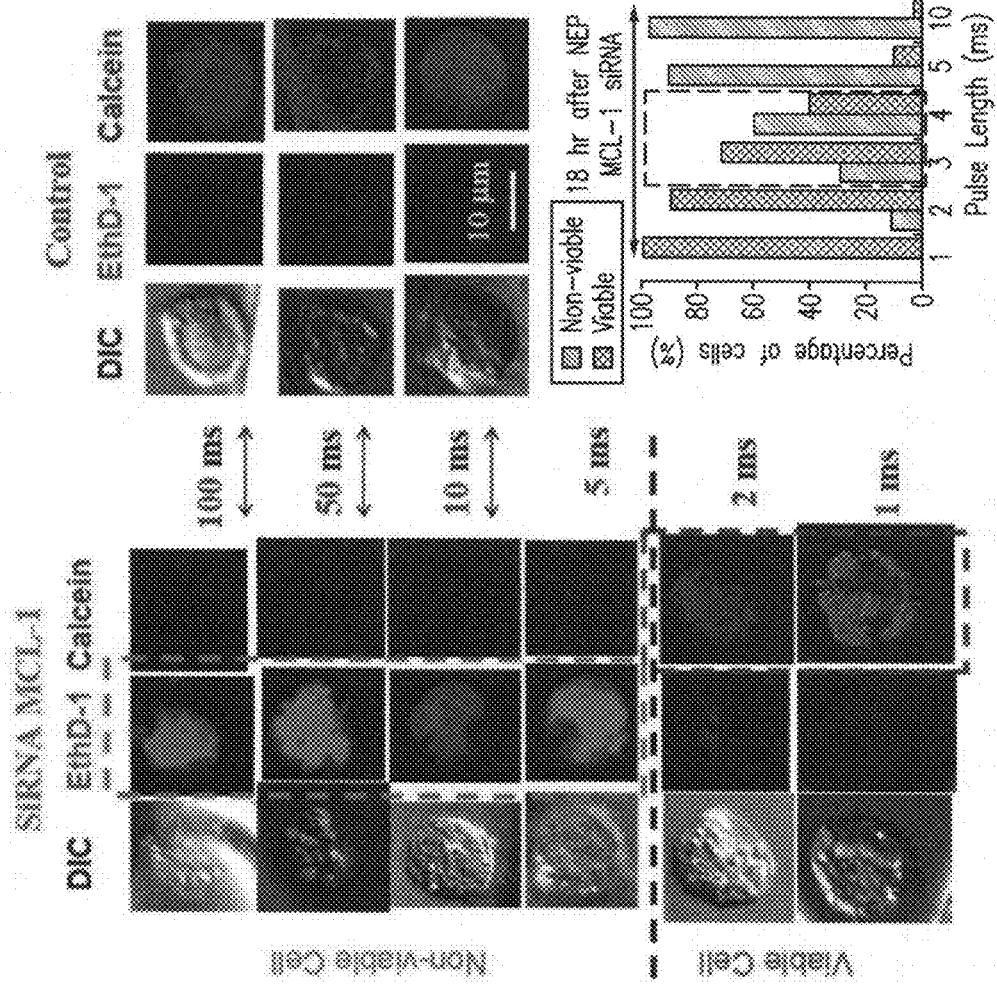
FIG. 10 shows data from studies where K562 cells were treated with different doses of siRNA(Mcl-1)

The dosage effect on transfecting K562 cancer cells with siRNA(Mcl-1) was studied. The anti-apoptotic protein Mcl-1 promotes the survival of lymphocytes and hematopoietic stem cells and is linked to drug resistance and poor treatment outcomes in many tumor types. FIG. 10 shows NEP experiments that were conducted to determine the critical dosage of siRNA(Mcl-1) to kill K562 cells. When the pulse length is larger than 5 ms at 220 V/2 mm, a fatal dose of siRNA(Mcl-1) was delivered to cells (indicated by the red fluorescence). However, most cells remained viable when the pulse length was less than 2 ms (green fluorescence). Statistical variations of the critical dosage for individual cells were studied using NEP with the pulse length varying from 2 to 10 ms. 7-11 cells were tested for each pulse length. FIG. 10 summarizes the percentages of viable and dead cells. A parallel set of transfections using the same pulsing parameters but a scrambled siRNA is shown in the "control" columns. None of these resulted in cell death. In FIG. 10 differential interference contrast (DIC) microscopy images are shown in the left column. The green live/red dead fluorescence signals were from a viability/cytotoxicity assay 18 hr after transfection with two probes that measure intracellular esterase activity and plasma membrane integrity. For NEP pulse durations of 5 ms or longer, the injected siRNA down-regulated the Mcl-1 protein sufficiently to induce apoptosis in K562 cells. On the right, all cells transfected with a scrambled siRNA sequence remained alive. The lower right shows cell viability under different pulse durations of siRNA(Mcl-1) injection at 220 V/2 mm (Pulse length (PL)=1 ms, number of cells (N)=10; PL=2 ms, N=9; PL=3 ms, N=7; PL=4 ms, N=7; PL=5 ms, N=8, PL=10 ms, N=11).

Example

GFP Plasmid (3.5 kbp) Transfection by NEP

Figure 11:
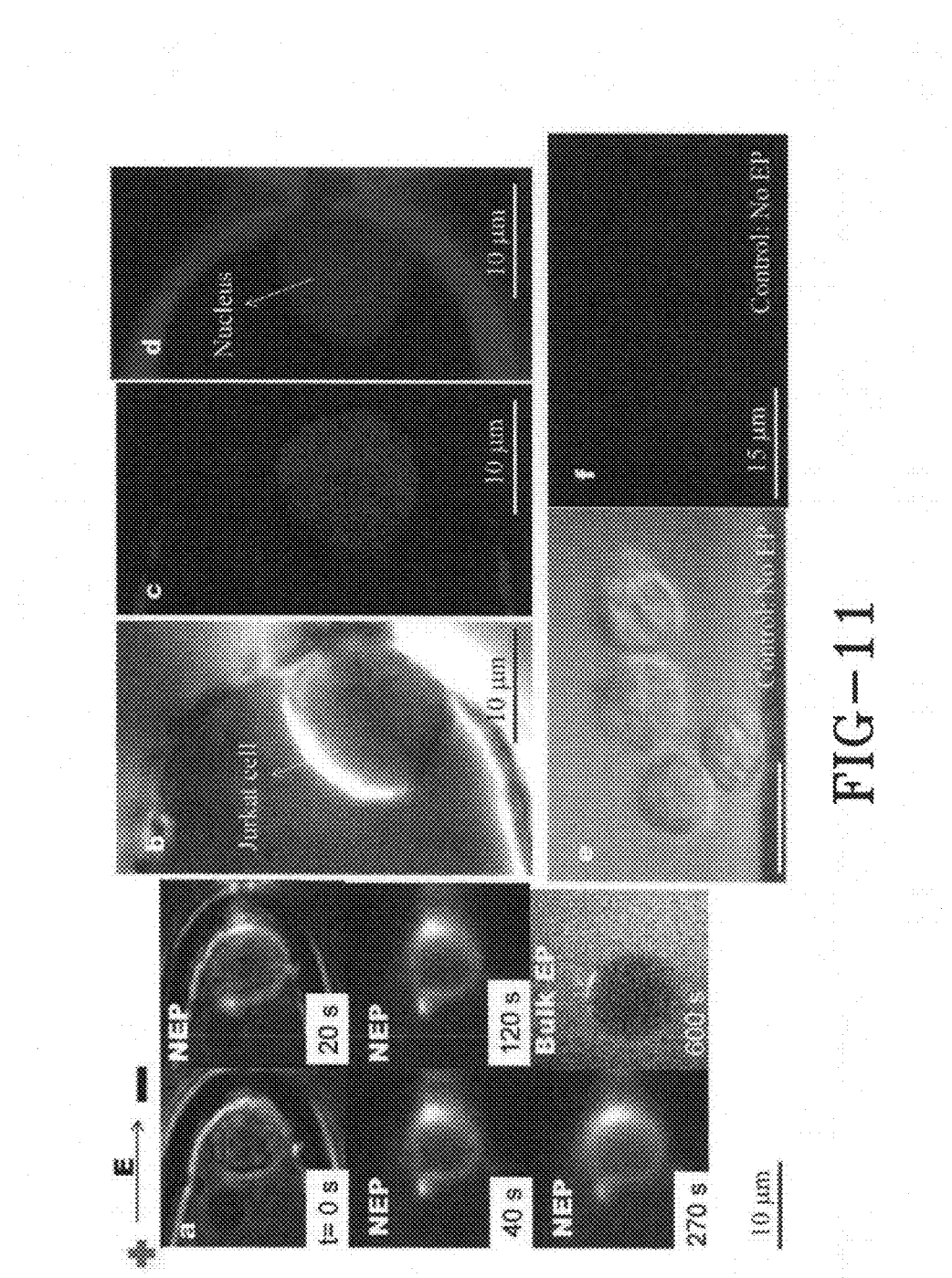
FIG. 11 shows the results when a cy3-labeled GFP plasmid (3.5 kbp, 0.05 µg/µl) was used as a large reporter gene to visualize and detect the gene transfection process in the NEP device.

FIG. 11a-f shows the results when a cy3-labeled GFP plasmid (3.5 kbp, 0.05 μg/μl) was used as a large reporter gene to visualize and detect the gene transfection process in the NEP device. A single Jurkat cell was isolated and held close to the nanochannel tip pre-filled with the cy3-labeled plasmid DNA. Then, three pulses of 250 V/2 mm with 10 ms duration were applied to transfer the plasmid DNA into the cell. Before EP, there is no evidence of any fluorescence at the cell membrane FIG. 11a. When three electric pulses were applied, some labeled-plasmid appeared at the cell membrane by the localized electro-permeablization. With increasing time to 40 s, more labeled plasmid molecules were internalized into the cytoplasm. The fluorescent intensity remained constant in the cell after 40 s but gradually diffused inside the cytoplasm in 120-270 s. In comparison, a smaller number of the plasmid DNA molecules were observed at the cathode side of the cell in the case of single cell bulk EP experiments under the same EP settings. There was little changes 600 s after EP. It has been reported that at least 30 min was required to transfer plasmid-DNA inside the cytoplasm by endocytosis in bulk EP. Clearly, disclosed NEP methods are more efficient to deliver large genes into cells. After plasmid transfection, the cell culture medium was added to the micro channels of the NEP chip. Then, the chip was placed in a small Petri dish and incubated at 37° C. with 5% $CO_2$. The GFP was detected in the entire cell 24 h after poration. In a control experiment, the cells and GFP plasmid were mixed in another nano-chip device and incubated for 24 h without any EP process. There was no green fluorescence in the control experiment. FIG. 11a shows the time series of cy3-labeled GFP plasmid (3.5 kbp) up-taking from 0 to 270 s, after NEP, in contrast to bulk EP at 600 s, FIG. 11b is the phase contrast image of the incubated cell at 24 h after NEP, FIG. 11c is the green fluorescence image and FIG. 11d the blue fluorescence image of cell nucleus stained with DRAQ-5 of the same cell, FIG. 11e the phase contrast image and FIG. 11f the green fluorescence image of incubated cells in the control experiment at 24 h.

Example

Comparison Transfection

Figure 12:
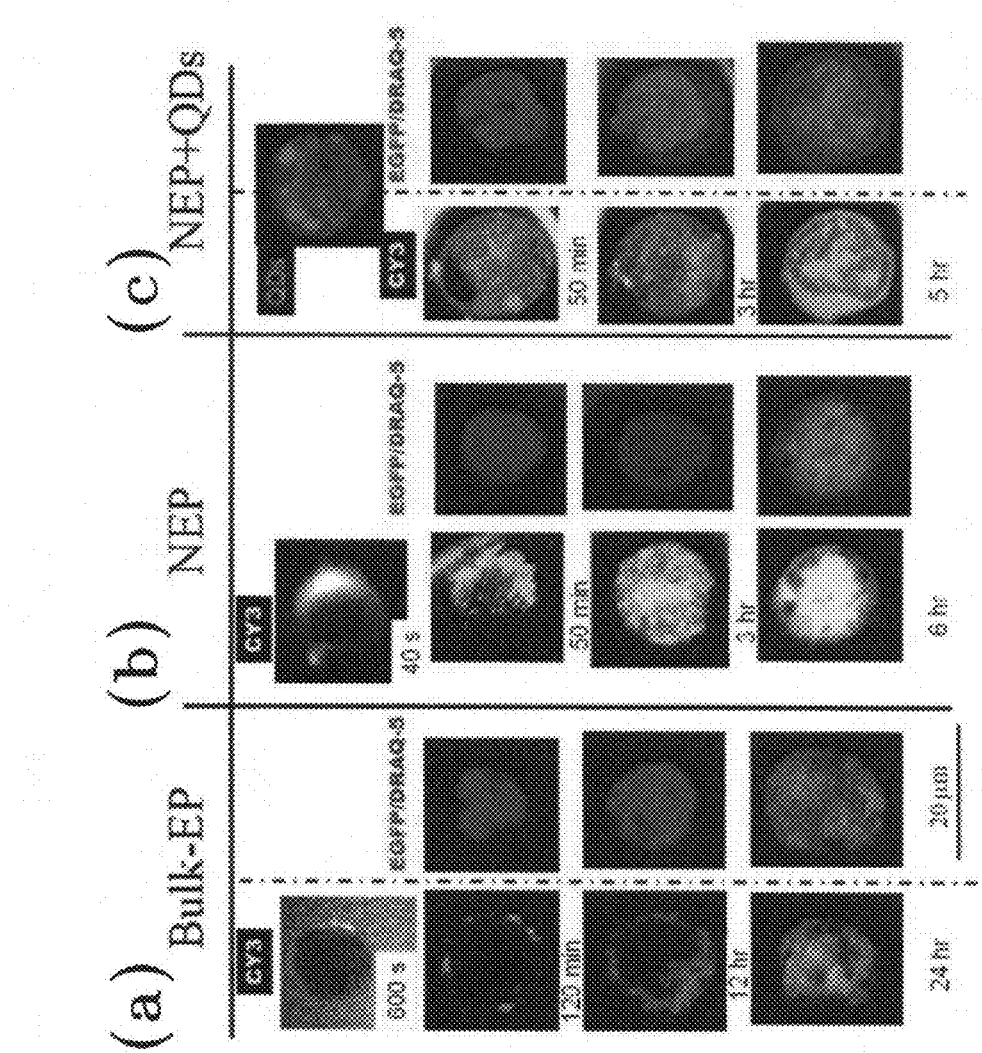
FIG. 12 shows data from transfection of Jurkat cells by a 3.5 kb Cy3-labelled GFP plasmid gene in a) a representative cell taken from a bulk EP run, b) NEP c) NEP+QDs.

To study NEP for larger transfection agents, a Cy3-labeled GFP plasmid (3.5 kb) was used to visualize the gene transfection process of Jurkat cells. Again, we contrast conventional BEP with NEP. In BEP, DNA "complexes" formed on the outside of the cell followed by an endocytosis-like passage into the cytoplasm that takes nearly an hour, FIG. 12a. This is similar to previously reported observations. Migration to the nucleus and subsequent transcription required many hours. GFP fluorescence was not observed even 12 hrs after transfection. On the other hand, NEP injects the plasmid directly into the cytoplasm: within 40 s of poration, a significant Cy3 fluorescence was observed inside the cell membrane. Migration of the DNA to the nucleus and transcription occurred under 6 hrs FIG. 12b. For higher gene transfection, nanoparticles such as gold or quantum dots (QDs) can be used to facilitate delivery, roughly analogous to the role of the needle in microinjection. FIG. 12c shows the NEP transfection of a Jurkat cell using a mixture of QDs conjugated with the COOH group with the aforementioned GFP plasmid. This procedure led to strong GFP expression within 3 hrs. FIG. 12c also shows that QDs were delivered uniformly inside the Jurkat cell using NEP. A viability/cytotoxicity assay, confirmed the transfected cells shown in the Figure to be alive. Injecting a uniform spatial distribution of nanoparticles into a cell is valuable for many scientific studies, but not achievable by BEP, MEP or other methods. In FIG. 12 Cy3 fluorescence is shown in the black and white photos taken shortly after transfection. In the color photos, the Cy3 fluorescence shows as yellow, the nucleus (DRAQ-5 fluorescence) is blue, and the GFP signal is green. On the left, it took nearly an hour for GFP to pass the cell membrane in bulk EP. GFP fluorescene was seen after 18 hrs. In the center, NEP injected DNA directly into the cytoplasm. GFP fluorescence was seen in 6 hrs. On the right, a mixture of plasmid and quantum dots facilitated delivery of DNA into cell nucleus. A strong GFP signal was seen within 3 hrs. QDs were delivered uniformly inside the cell. Bulk EP was carried out on NEON™ transfetcion system at 1325 V with 10 ms pulse length and 3 pulses. Two pulses of 260 V/2 mm with 5 ms pulse length and 0.1 separation were used in NEP.

Example

Q-Dots Up-Taking by NEP

Figure 13:
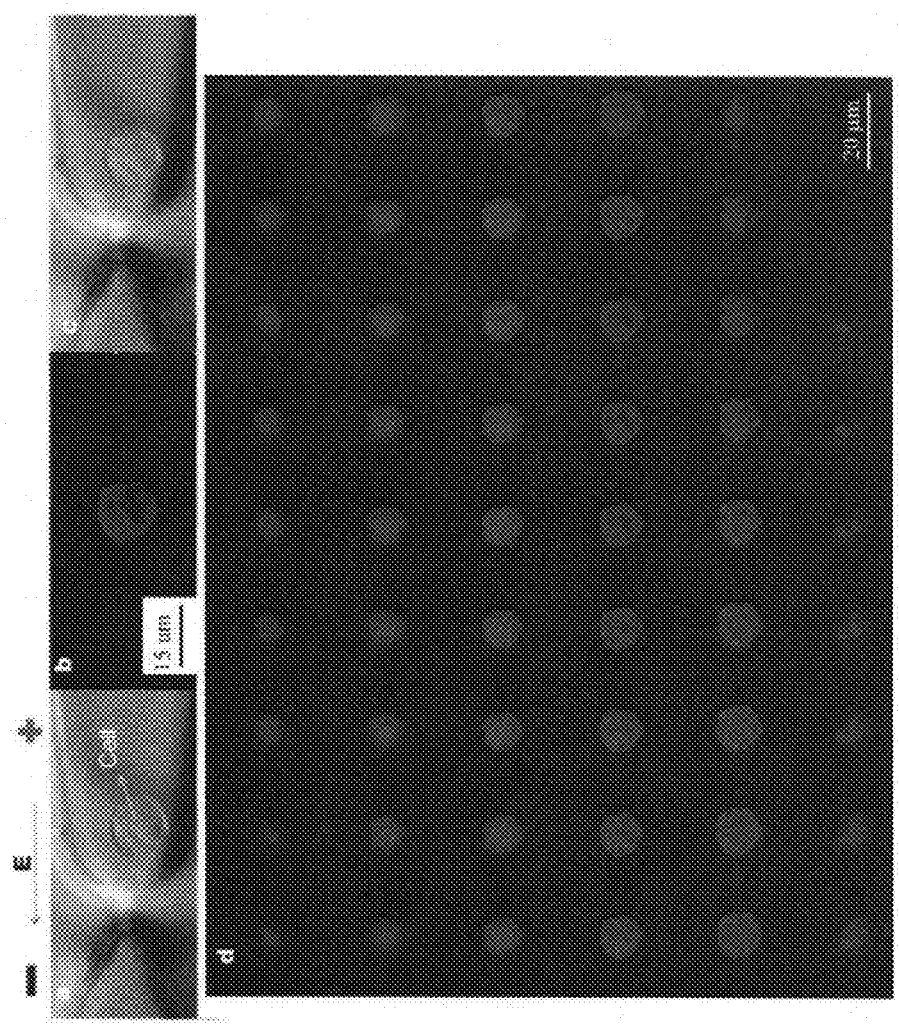
FIG. 13 shows (a) The phase contrast image, (b) the green fluorescence image, (c) the combined image of a transfected cell by Q-dots, and (d) the Z stacked confocal microscope image from bottom to top of the transfected cell with 0.2 J . . . 1m step size.

To explore the delivery of nanoparticles by NEP, Q-dots (Invitrogen Corp.) conjugated with the COOH group (8.0 nM) were introduced in the nano-chip device and transfected to a Jurkat cell by NEP using a single pulse of 250 V/2 mm with 25 ms duration. FIG. 13 summarizes the results from the Q-dots up-take by NEP to Jurkat cell. Many Q-dots can be tracked inside the transfected cell as shown in FIG. 13a-d. FIG. 13a shows the phase contrast image, (b) the green fluorescence image, and (c) the combined image of a transfected cell by Q-dots, (d) the Z stacked confocal microscope image from bottom to top of the transfected cell with 0.2 µm step size.

Example

Plasmid Transfection

Figure 14:
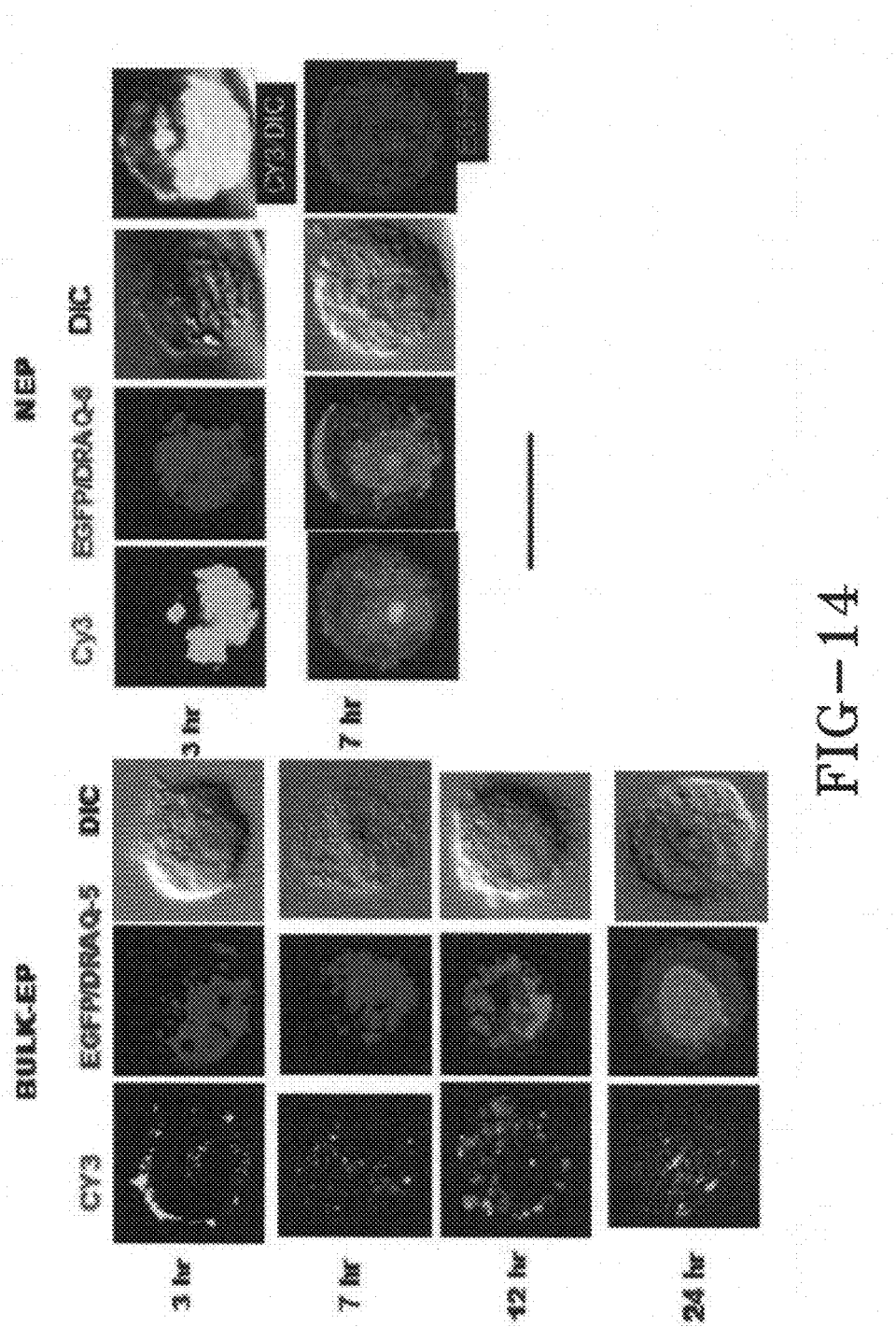
FIG. 14 shows BEP transfection of pCAG-EGFP (7 kbp) conjugated with CY3 inside MEF. NEP transfection of MEF cells by larger plasmid pCAG-GFP-CY3 at 3 pulses of 230 V with pulse durations of 5 ms and 0.1 s separation.

To investigate the capabilities of an NEP platform for transecting cells with large plasmids, such as cell reprogramming factors the NEP delivery of pCAG-GFP plasmids (~7 kbp) into mouse embryonic fibroblast (MEF) cells as a model system was examined. FIG. 14 compares the delivery of pCAG-EGFP by BEP (Neon™ transfection system, one pulse at 1300 V, pulse duration=30 ms) and NEP (three pulses at 220 V, pulse duration=5 ms, separation between pulses=0.1 s). In BEP, Cy3-plasmids were delivered by an endocytosis-like passage into the cytoplasm that took several hours (FIG. 14, left). After 12 hours of BEP transfection, a weak GFP fluorescence signal was detected[13]. On the other hand, NEP transferred large plasmids directly into the cytoplasm (FIG. 14, right) by NEP. Strong green fluorescence expression of pCAG-GGFP was detected inside MEF after 7 hours of NEP transfection.

To handle large numbers of cells, a high throughput process is needed for NEP. Centrifugation has been widely used in the biomedical field for cell and biomolecule separation.

FIGS. 15a-b show two exemplary designs. In contrast to the optical tweezers based NEP chip, four reservoirs are used in this design, two for the transfection agent (e.g. DNA, molecular probe or nanoparticles) and two for the cell. The length of the cell-side microchannels is greatly shortened to allow only one cell per microchannel. The chip is sealed similar to the optical tweezers device. The cell loading and de-loading process includes seven steps: 1) Load biomolecules using the same method as used for optical tweezers devices and load cells to one of the cell reservoirs using a pipette. 2) Place the chip near the periphery of a disk that is mounted on a rotation device. (3) Move the cells from the cell reservoir to the main connection channel by using the centrifugal force at a low rotation speed. Excess cells will flow to the other cell reservoir. The biomolecule side needs to be completely sealed to prevent any material loss. (4) Demount the chip rotate it 90 degrees and remount it to the disk in order to alter the direction of the force so as to push the cells into the microchannels. Move the cells to the end of the cell-side microchannels by using the centrifugal force at a higher rotation speed. This action also pushes cells against the tip of the nanochannels to ensure good cell-channel contact. Conduct electroporation. (6) Add Trypsin to the cell side to release the cells from the microchannel surface. (7) Turn the chip around on the disk surface and use the centrifugal force to de-load cells into the original cell reservoir.

Figure 16:
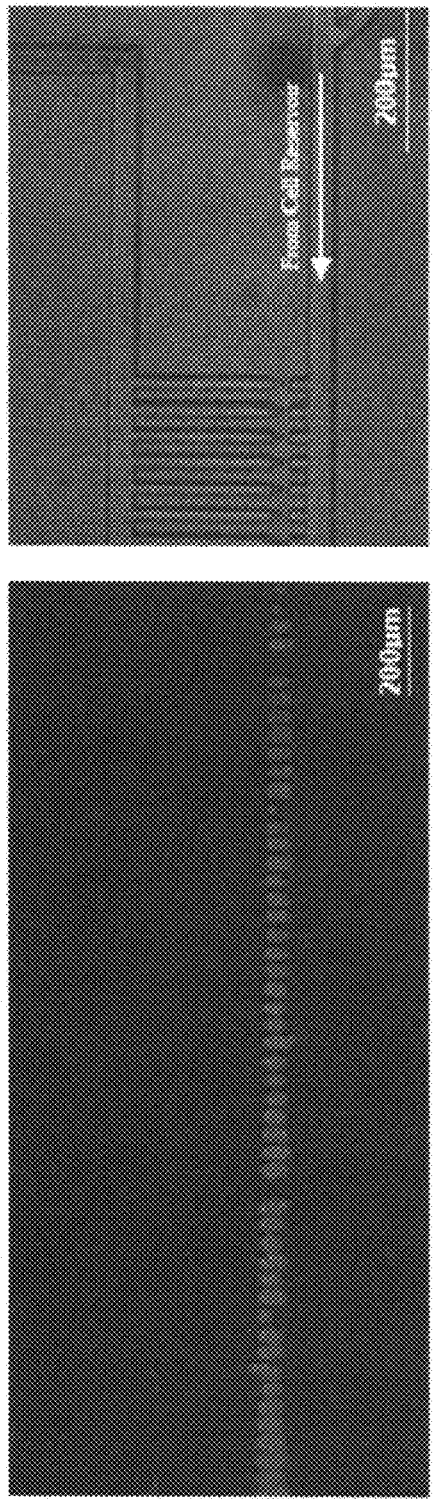
FIG. 16 is a (a) fluorescence image showing A549 cells loaded into 300 microchannels after applying 100 g centrifugal force for 2 minutes; (b) design of centrifuge chip prototype used in cell loading.
Figure 17:
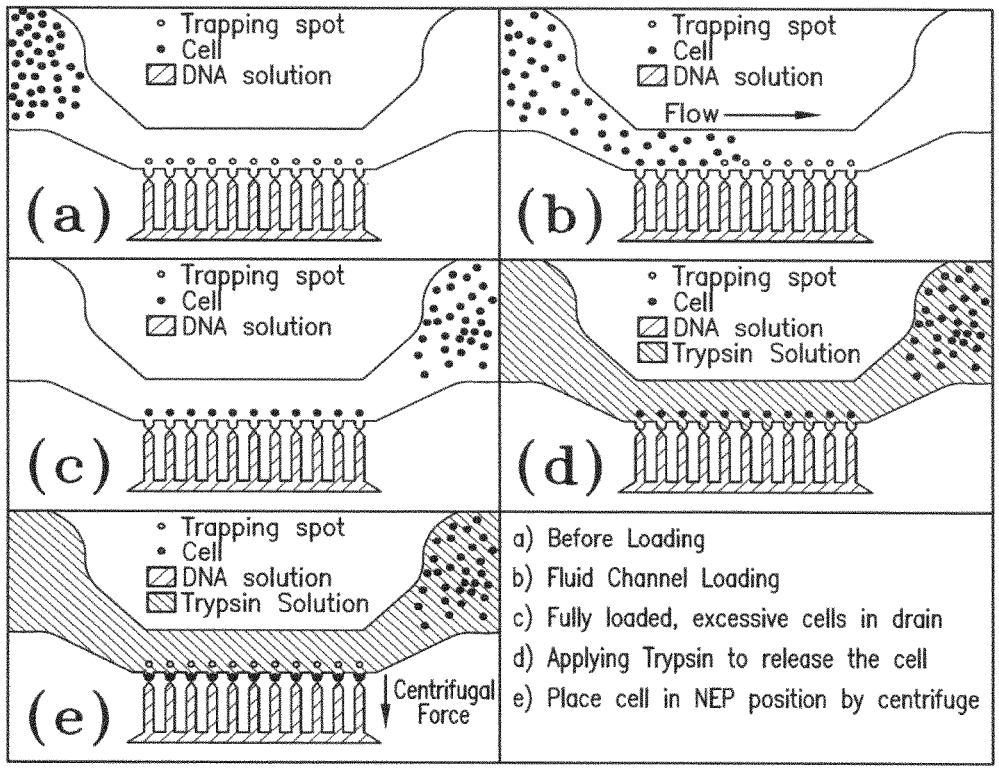
FIG. 17 is a schematic of the cell loading procedure on multicell NEP chip with trapping spots.

FIG. 16 shows a result in which ~200 cells are transfected within a few minutes. Although several microchannels did not receive any cells and some channels got more than one cell, the electrical behavior of each microchannel will be the same with or without cell(s) because the major electric resistance (and thus the voltage drop) is across the nano-channel. This simple and fast approach demonstrates the feasibility of a high throughput NEP. Alternatively, for example, a cell trapping spot can be deposited in front of each microchannel in the main connection channel as shown in FIG. 17.

In an embodiment, this cell trapping spot can be tethered antibody molecules to capture exactly one cell per microchannel during the cell loading stage. Excess cells can be washed away from the main connection channel. By using trypsin to release the cells from the trapping spots, each cell can move into the microchannel opposite it using centrifugal force.

Figure 15:
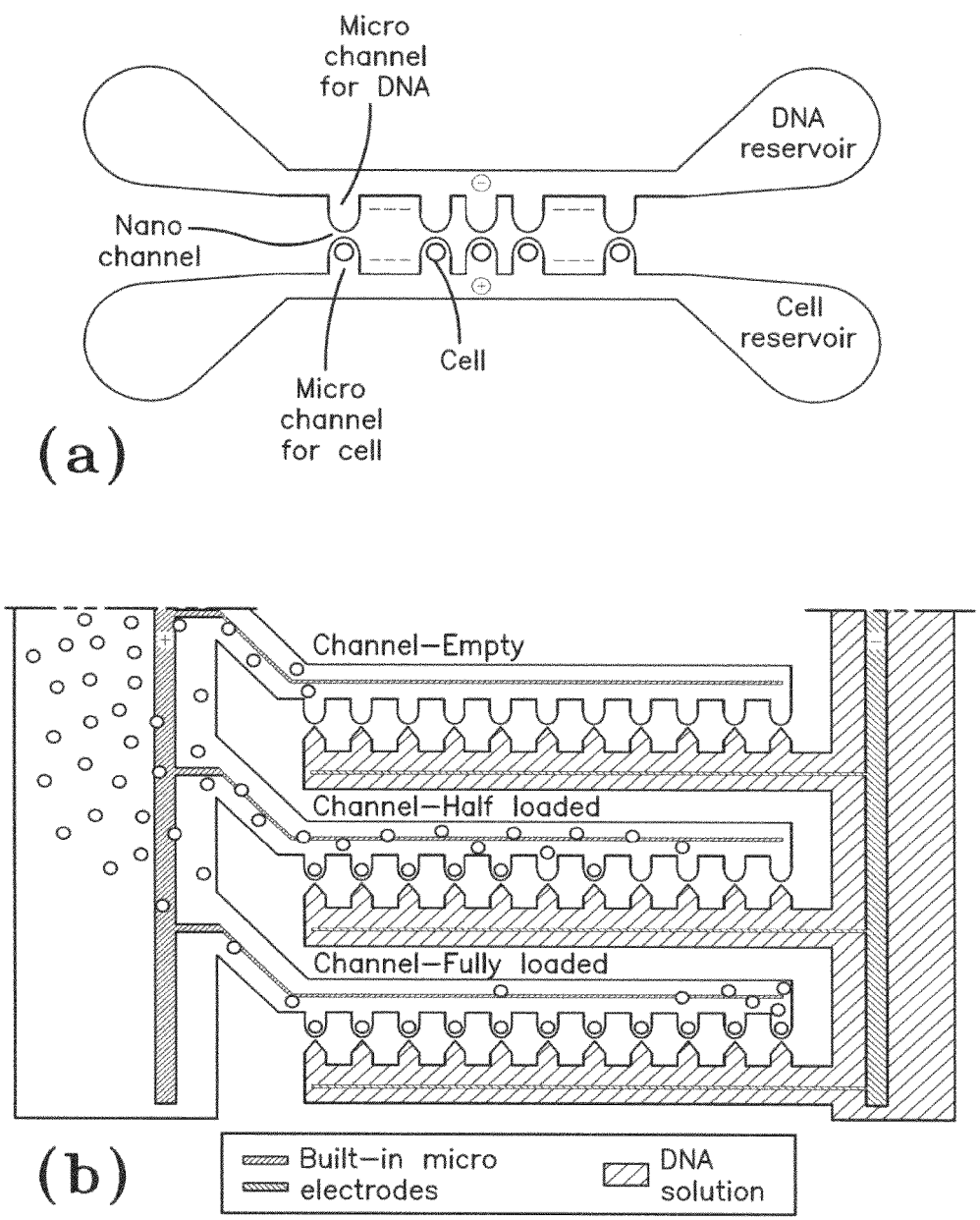
FIG. 15 is a schematic of centrifugation based high throughput NEP: (a) single array chip design; (b) multi-array chip design and cell loading process.

The current microchannel-nanochannel-microchannel NEP array shown in FIG. 15 can hold 200-300 cells and it can be extended to 1,000 cells. By adding multiple arrays on a single chip and placing a number of chips on one rotation disk, a large cell population (i.e. from 10,000 to >50,000) can be porated uniformly and simultaneously using NEP. Although the aforementioned high throughput microchannel-nanochannel-microchannel NEP array' chip still cannot compete with the conventional bulk electroporation methods in regard to cell numbers ($10^4$ vs. $10^6$) and assay time (minutes vs. seconds), the unique features of high precision dosage control and fast and high efficacy transfection (i.e. bypassing endocytosis and endosome escape) provided by NEP may often more than offset these limitations.

Example

Modeling

Figure 18:
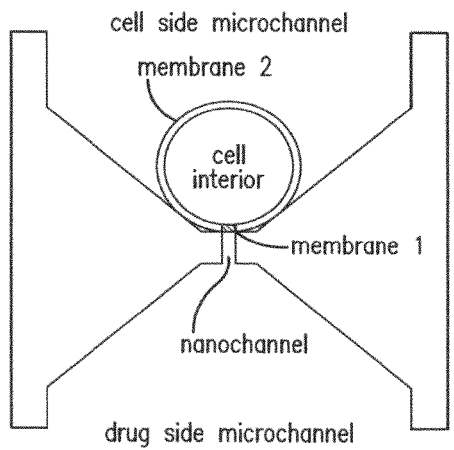
FIG. 18 is a schematic of a NEP device.

As a representative example, NEP transfection of a 15 µm diameter cell by COOH conjugated quantum dots with a total diameter 20 nm was modeled. A single 10 ms, 200 V pulse is used in the model. FIG. 18 shows a schematic of the experimental layout. The nanochannel is a 90 nm diameter and 3 µm long channel. The conductivity of the PBS solution used for the experimental work is 1.5 S/m. This is reduced to 0.8 S/m by the addition of the low conductivity solution containing the quantum dots. The microchannels are about 40 μm diameter and 1000 μm long. Thus the resistance is: $R_{nc}=1/G_{nc}=(\sigma_{buffer}A/l)^{-1}=590$ MΩ. The microchannels are about 40 um diameter and 1000 um long giving a resistance $R_{MC}=1$ MΩ. This is negligible compared to the nanochannel and relevant cell membrane resistances. Thus, the microchannel is modeled as wires, treat the fluids in the microchannels as equipotential surfaces and note that variations in the placement of the electrodes have negligible impact on the process. The cell interior will be treated as an equipotential surface. The cell membrane is divided into two parts as shown in FIG. 18. Membrane 1 refers to the section adjacent to the nanochannel and membrane 2 is the rest of the cell membrane. Transverse conduction within the cell membrane between the two sections is ignored. Electrically an intact cell membrane is modeled as a resistance in parallel with a capacitance. Membrane surface capacitances are more reliably known: $1\times10^{-2}$ F/m$^{-2}$. For the present conditions, the resistance and capacitance of membrane 1, adjacent to the nanochannel are $8\times10^{13}$Ω and $6\times10^{-17}$ F respectively. Membrane 2 has resistance and capacitance of 710 MΩ and 7 pF respectively. Putting all of these together produces the electrical model of the system for an intact cell. Note: the applied voltage satisfies: $V_{applied}=V_{NC}+V_{TM1}+V_{TM2}$. This model is valid so long as all of the membranes remain intact. In visualizing the NEP process the exact value of this minimum threshold doesn't matter very much—somewhere between 0.2 V and 5 V.

In this model the NEP process is readily described. Upon application of a voltage pulse, almost instantly all of the voltage appears across membrane 1, facing the nanochannel. That membrane reaches the critical voltage in nanoseconds and porates. Assuming that the now-porated membrane 1 represents a very low resistance, the second "outer" membrane starts charging in a predictable way:

$$V_{TM2}=V_{applied}R_2/(R_2+R_{NC})(1-e^{-t/(R_{NP}C_2)})\approx 0.54 V_{applied}(t/4.1)$$

where t is measured in milliseconds. This predicts that for a high voltage pulse (100 V or greater), the second membrane charges to a critical voltage in 10's to 100's of microseconds and must, in this model porates. Again, assuming that the $2_{nd}$ porated membrane has a negligible voltage drop across it, the "poration current" flowing through the cell is limited by the nanochannel: $I\approx V_{applied}/R_{NC}$ Electrophoresis dominates the transport of the transfection agents through the nanochannel. This is a feature that is novel to NEP because of the high fields used. Since almost all of the voltage drop is across the nanochannel, the field in the channel is very nearly pulse voltage divided by the channel length. For these conditions, this is about 70 MV/m. We use for the mobility of the quantum dot (QD), $\mu_{QD}=-1\times10^{-8}$ m$^2$V$^{-1}$ s$^{-1}$ which produces a drift velocity for the QD of about 700 μm/ms. Thus transfection transport occurs as follows. QDs enter the nanochannel through a combination of drift and diffusion and are rapidly, within a few microseconds, swept to the cell. In the numerical simulations it is shown that fringe fields extend into the cell and can "inject" QDs through the cell membrane and into the cytoplasm.

The fields generated during NEP are truly enormous—several tens of MV/m. Experimentally, a striking feature of the data is that, in contrast to what is observed in other types of EP, for NEP large transfection agents—DNA and QDs—appear almost instantly inside the cytoplasm. This suggests that large pores are created in the cell membrane if not the complete breakdown/disappearance of the membrane opposite the nanochannel during the electrical pulse.

It is clear that pores will form in the cell membrane near the nanochannel tip at high enough voltages. Those pores allow the passing of biomolecules into the cell attached to the nanochannel during poration.

To further analyze the NEP process and to compare NEP and MEP, finite element simulations of the electrostatic problem were carried out. The analysis is based on the setup for cell EP depicted in FIG. 18. The problem is simplified to be axial symmetrical. From the top view, the channel for EP with diameter d=90 nm and length l=3 μm is embedded between two larger microchannels with width W=40 μm. A cell with diameter D=15 μm is placed at the end of left microchannel. An electric potential, Vp=200 V, is applied across the whole device of total length L=2 mm. The table below includes values for additional model parameters. The electrostatic problem was solved to study the cell's transmembrane potential (TMP), material dynamics in the channel during EP, and the electric field at various points within the apparatus and the cell itself.

| Symbol | Value | Definition |
|---|---|---|
| D | 15 μm | Cell diameter |
| $d_m$ | 5 nm | Cell membrane thickness |
| $\sigma_e$ | 0.8 S/m | Electrical Cond. of external medium |
| $\sigma_i$ | 0.2 S/m | Electrical cond. Of cytoplasm |
| $\sigma_m$ | $5\times10^{-1}$ S/m | Electrical cond. Of cell membrane |

For a cell with no net surface charge, the static electric field is governed by the Laplace equation:

$$\nabla\times(\sigma\nabla V)=0$$

where V is the electric potential and σ is the electric conductivity. Once V is solved, the electric field E could be determined by $E=-\nabla V$ and TMP $V_m$ can be obtained from $V_m=V(S_{ext})-V(S_{int})$ where S is the surface of cell membrane and "ext" and "int" denote the external and internal surfaces. To circumvent the difficulty in the mesh generation for the thin cell membrane, the concept of contact resistance in heat conduction is adopted here. The computer simulation is carried out using commercial FEM software, COMSOL Multiphysics™.

Figure 19:
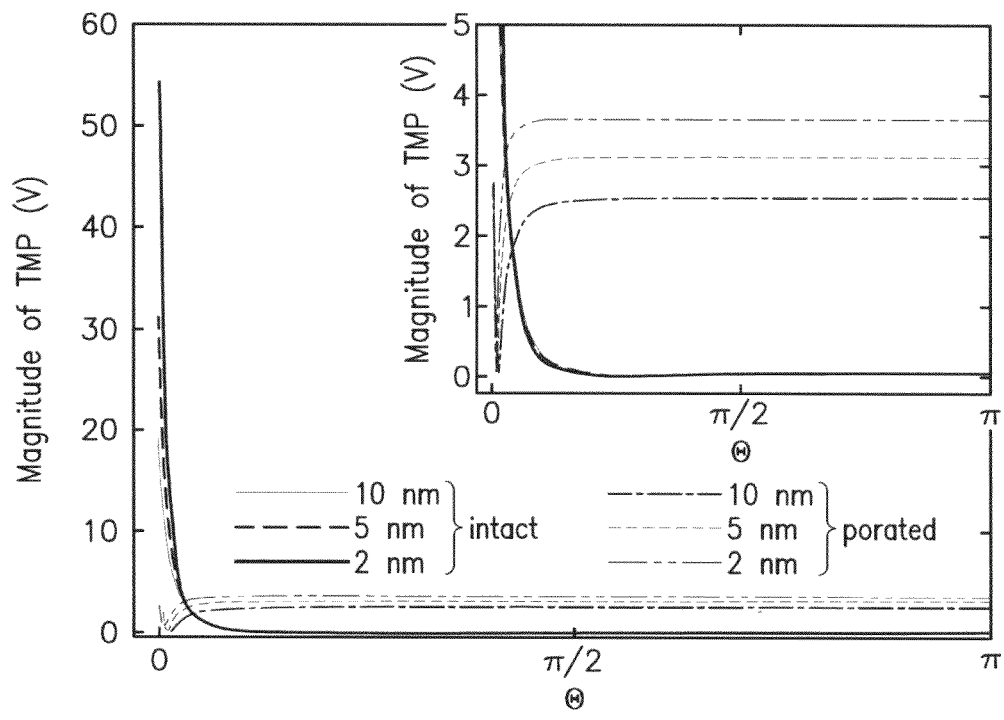
FIG. 19 is a graph of transmembrane potentials for different cell-nanochannel gaps.

To study the sensitivity of cell placement in NEP, a gap between the cell edge (θ=0) and the outlet of the nanochannel is included in the simulation. Gap sizes of 10, 5, and 2 nm were studied. Simulations were performed both for systems with intact cells and for systems containing a pore at the interface with the nanochannel. A single pore was created on the cell whose area was that defined by the contact surface with the 90 nm diameter cylinder of the nanochannel. In the simulation, the pore on the cell is a section of the membrane with higher electric conductivity, 0.2 S/m. FIG. 19 shows the magnitude of TMPs of the cell without and with the pore with an enlarged view at the low voltage in the inserted. If the cell is intact (solid lines), the max(TMP) increases from 20 to 55 V as the gap is decreased from 10 to 2 nm. Therefore, before the cell is electroporated, the peak of TMP is indeed sensitive to the cell position. However for all values, the cell membrane would certainly porate; nanopore(s) would be formed within microseconds once the TMP is over a critical value. As a result, the sharply peaked distribution of TMP lasts an extremely short time compared to the total electroporation pulse length (several milliseconds). After the cell is electroporated, the peak TMP will drop dramatically and the TMP for the area away from the defect will increase (solid lines to dashed lines). The sharply peaked TMP distribution changes to being near-uniform except for the area of the pore itself. After the cell is electroporated by the nanochannel the sensitivity to the gap is reduced. The exact position of the cell is unimportant in the sense that for all 3 positions, a 200 V pulse should be more than enough to cause electroporation.

Figure 20:
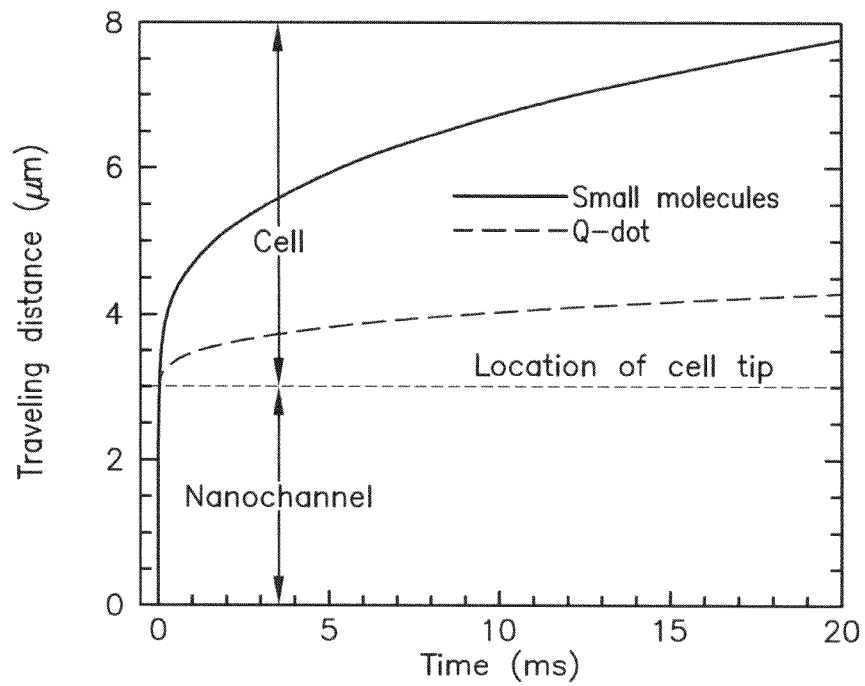
FIG. 20 is a graph showing transport of transfection agents into a cell.

The transport of transfection agents was also modeled. To do this the computed electric field was taken and numerically integrated the equation of motion for a molecule traveling down the center of the nanochannel. It was assumed that the transfection agent passed unimpeded through the cell membrane. Within the cell itself the quantum dot mobility was reduced by a factor of 60. This is consistent with measured reduction of the quantum dot diffusion coefficient relative to that of water. The simulation reproduces the observation of the circuit-based model, above, that molecules are rapidly transported through the 3 μm long nanochannel. In addition, we observe that fringing fields electrophoretically "inject" charged particles a significant distance past the cell membrane and into the cytoplasm. FIG. 20 shows the results.

Precise dose control in the absence of cell damage is nearly impossible with conventional techniques. However, These requirements can be easily achieved using NEP, but not MEP for the following four reasons. (1) The cell surface area affected by electroporation in NEP is less than 1% that in MEP, leading to much less damage to the cell. This is particularly critical for small primary cells. (2) In NEP the "shot" is generated by the large electrophoretic force imposed on the to-be-delivered biomolecules both within the channel and through the cell membrane. For this purpose, a high electric voltage is necessary to generate a large electric field and a correspondingly high electrophoretic force. Dose control is achieved because transport of transfection agents is dominated by electrophoresis occurring during the electrical pulse. In comparison, voltages used in MEP result in low electric fields within the microchannel and cannot produce meaningful electrophoretic forces. Consequently, for MEP, delivery of biomolecules into the cell still has to rely largely on molecular diffusion and endocytosis after poration. If a higher voltage (say hundreds volts) was used in MEP to increase molecule acceleration, the cells would not survive. (3) Although the electroporation duration is very short (ms), the formed pores on the cell membrane may take many seconds to re-seal. To prevent cell damage caused by ions leaking out of the cell during and after poration and poor dosage control caused by uncontrolled biomolecules taken up by the cell after poration, molecular diffusion through the channel during and after poration must be minimized. Mass diffusion through a channel is inversely proportional to the channel area ($d_2$) and exponentially proportional to the inverse of the channel length squared (i.e. $\sim\exp(\alpha t//_2)$). A nanochannel (<100 nm) is able to limit mass diffusion much better than a microchannel (>1 μm). For large molecules such as nucleic acids, the Brownian motion and steric hindrance further limit the transport of molecules through the very small nanochannels. (4) The precision of cell placement around the channel plays a major role on the delivered dosage. For MEP, a portion of the cell often deforms into the channel under a force (either vacuum or hydrodynamic). In some cases, particularly for smaller primary cells, the whole or a major portion of the cell is squeezed into the channel. It is difficult to keep the cell deformation and shape the same for each microchannel. This is not an issue for microchannel-nanochannel-microchannel NEP design because the cell placement and cell shape can be kept consistent as long as the cell is in close contact with the nanochannel tip and there is virtually no cell deformation.

When K562 cells were drawn into microchannels they confirmed nicely onto the microchannel surface in close contact with the nanochannel tip in an exemplary NEP device when loaded using optical tweezers. The cell placement and shape remained unchanged hours after poration. Precision of cell placement is critical for repeatable dosage controlled delivery to individual cells. The repeatable transfection and dose control in NEP indicates that it can reliably and accurately position cells with respect to the nanochannel tip.

The terms "a" and "an" and "the" and similar references used in the context of describing the disclosed embodiments (especially in the context of the following claims) are to be construed to cover both the singular and the plural, unless otherwise indicated herein or clearly contradicted by context.

Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the disclosed embodiments and does not pose a limitation on the scope of the disclosed embodiments unless otherwise claimed. No language in the specification should be construed as indicating any non-claimed element essential to the practice of the disclosed embodiments or any variants thereof.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability.

Preferred embodiments of this invention are described herein, including the best mode known to the inventors for carrying out the invention(s). Of course, variations on the disclosed embodiments will become apparent to those of ordinary skill in the art upon reading the foregoing description. The inventors expect skilled artisans to employ such variations as appropriate, and the inventors intend for the invention(s) to be practiced otherwise than specifically described herein. Accordingly, this disclosure includes all modifications and equivalents of the subject matter recited in the claims appended hereto as permitted by applicable law. Moreover, any combination of the above described elements in all possible variations thereof is encompassed by the disclosed embodiments unless otherwise indicated herein or otherwise clearly contradicted by context.

Having shown and described an embodiment of the invention, those skilled in the art will realize that many variations and modifications may be made to affect the described invention and still be within the scope of the claimed invention. Additionally, many of the elements indicated above may be altered or replaced by different elements which will provide the same result and fall within the spirit of the claimed invention. It is the intention, therefore, to limit the invention only as indicated by the scope of the claims.

What is claimed is:

1. A method for transfecting cells, comprising the steps of:
providing a nanochannel electroporation device, the device comprising an array of transfection sites, each transfection site having a first microchannel, a second microchannel and a nanochannel having a first opening at the first microchannel and a second opening at the second microchannel, the nanochannel connecting and extending between the first and second microchannels;
providing, in the respective first microchannels of the array, a transfecting agent;
loading, in the respective second microchannels of the array, a cell to be transfected, the cell positioned at the second opening of the respective nanochannel; and
applying a voltage, in excess of 200 V, across the nanochannel.

2. The method of claim 1, wherein:
applying the voltage transfects the cell with a predetermined dose of the transfecting agent.

3. The method of claim 2, wherein:
the voltage is applied for milliseconds to transfect the cell with an error of the dose of less than 20%.

4. The method of claim 1, wherein:
the transfecting agent is chosen from the group consisting of plasmids, biomolecules, fluorophores, dyes, RNA, DNA, and proteins.

5. The method of claim 1, wherein:
the cell is viable after transfection.

6. The method of claim 1, wherein the loading step is achieved by applying a centrifugal force.

7. The method of claim 1, wherein the loading substep is achieved by optical tweezers.

8. The method of claim 2, wherein:
a pulse number and duration of the voltage applied determines an amount of the predetermined dose transfected.

9. The method of claim 1, wherein the nanochannels in the array of transfection sites are laterally ordered and each nanochannel defines an axis, with the first and second microchannel connected to each nanochannel aligned with the axis.

10. The method of claim 2, wherein the transport of the transfecting agent across the nanochannel is dominated by electrophoresis occurring during the step of applying voltage across the nanochannel.

* * * * *